United States Patent
Ferrise et al.

(10) Patent No.: US 7,778,699 B1
(45) Date of Patent: Aug. 17, 2010

(54) SYSTEM AND METHOD FOR TRIGGER-SPECIFIC RECORDING OF CARDIAC SIGNALS USING AN IMPLANTABLE MEDICAL DEVICE

(75) Inventors: Gianni Ferrise, Huntington Beach, CA (US); Gregory Roberts, Los Angeles, CA (US)

(73) Assignee: Pacesetter, Inc., Sylmar, CA (US)

( * ) Notice: Subject to any disclaimer, the term of this patent is extended or adjusted under 35 U.S.C. 154(b) by 622 days.

(21) Appl. No.: 11/740,720

(22) Filed: Apr. 26, 2007

(51) Int. Cl.
*A61B 5/0432* (2006.01)

(52) U.S. Cl. .................. 600/523; 607/59; 607/62; 600/513; 600/522

(58) Field of Classification Search ................ None
See application file for complete search history.

(56) References Cited

U.S. PATENT DOCUMENTS

| | | | |
|---|---|---|---|
| 5,074,308 A | 12/1991 | Sholder et al. | |
| 5,431,691 A | 7/1995 | Snell et al. | |
| 5,707,398 A | 1/1998 | Lu | |
| 5,908,392 A * | 6/1999 | Wilson et al. | 600/509 |
| 6,249,705 B1 | 6/2001 | Snell | |
| 6,633,776 B2 | 10/2003 | Levine et al. | |
| 6,647,295 B2 | 11/2003 | Florio et al. | |
| 2007/0255155 A1* | 11/2007 | Drew et al. | 600/523 |
| 2008/0183085 A1* | 7/2008 | van Oort et al. | 600/508 |

* cited by examiner

*Primary Examiner*—Kennedy J Schaetzle

(57) ABSTRACT

Techniques are provided for controlling the recording of intracardiac electrograms (IEGMs) within an implantable medical device such as a pacemaker, wherein the device is capable of recording different channels of IEGMs in response to different diagnostic triggers. Exemplary triggers include pacemaker-mediated tachycardia; atrial tachycardia, atrial fibrillation, ventricular tachycardia, etc. In one example, the device stores, for each diagnostic trigger, a physician selection of particular IEGMs to be recorded for subsequent review. Then, whenever a trigger is detected, the device senses and records only the particular IEGMs that had been selected by the physician for that particular trigger. The IEGMs are eventually transmitted to an external programmer for review. In this manner, the physician can specify particular IEGMs to be stored in response to particular diagnostic triggers, thereby providing considerable diagnostic flexibility, while also conserving memory. Triggers can be classified as atrial-related or ventricular-related, with appropriate IEGMs stored. Pre-trigger IEGM storage can also be accommodated.

16 Claims, 12 Drawing Sheets

SYSTEM AND METHOD FOR TRIGGER-SPECIFIC RECORDING OF CARDIAC SIGNALS USING AN IMPLANTABLE MEDICAL DEVICE

FIELD OF THE INVENTION

The invention relates generally to implantable medical devices such as pacemakers and implantable cardioverter defibrillators (ICDs) and in particular to techniques for controlling the recording of intracardiac electrograms (IEGMs) and other diagnostic data therein.

BACKGROUND OF THE INVENTION

Implantable medical devices are often configured to be used in conjunction with an external programmer that allows a physician to display information detected by the implanted device. For example, the external programmer may operate to display electrical cardiac signals detected by the implantable device in the form of IEGMs. An IEGM is representative of electrical signals emitted by active cardiac tissue as detected by electrodes placed in, on or near the heart. The electrical signals are digitized and recorded within the implanted device along with an indication of the date and time, and are ultimately transmitted to the external programmer for display thereon, typically during follow-up sessions with the physician sometime after the device has been implanted.

The implanted device may also be configured to detect various events within the electrical cardiac signals, such as atrial depolarization events (P-waves), ventricular depolarization events (R-waves), ventricular repolarization events (T-waves), premature atrial contractions (PACs) and pre-ventricular contractions (PVCs), and to generate event codes representative of the events for transmission to the external programmer. The events are detected and event marker codes are stored in the implanted device along with the corresponding IEGM signals for subsequent transmission to the external programmer. The external programmer generates event marker icons based on the event code and displays the icons along with the IEGM signals and surface EKG signals. Exemplary event markers are: "P" for a sensed depolarization event in the atria; "R" for a sensed depolarization event in the ventricles; "A" for a paced depolarization event in the atria, and "V" for a paced depolarization event in the ventricles. Along with the event markers, the programmer may also display variable length horizontal lines representative of the length of atrial and ventricular refractory periods associated with certain events, as well as numerical values indicative of heart rate and indicative of various measured intervals between atrial and ventricular events, based on still further information recorded and transmitted by the implantable device.

Displays of IEGMs and corresponding event markers are helpful in permitting the physician to diagnose arrhythmias and to program the implanted device to provide optimal therapy. U.S. Pat. No. 5,431,691 to Snell et al. entitled "Method and System for Recording and Displaying a Sequential Series of Pacing Events" provides a description of the operation of an exemplary pacemaker and external programmer including a detailed description of the generation, transmission and display of IEGM data and event markers. See, also, U.S. Pat. No. 6,633,776 to Levine, et al., entitled "Method and Apparatus for Generating and Displaying Location-Specific Diagnostic Information using an Implantable Cardiac Stimulation Device and an External Programmer."

Herein, IEGMs, corresponding event markers and any other pertinent data stored therewith is collectively referred to as "IEGM data."

Current state-of-the-art devices permit IEGMs to be sensed and recorded using several possible electrode configurations. For example, one IEGM may be derived from voltage signals sensed between the right ventricular (RV) tip electrode and the RV ring electrode; whereas another IEGM may be derived from voltage signals sensed between the right atrial (RA) tip electrode and the housing or "can" of the device itself. Each electrode combination thereby provides a different "view" of the electrical conditions of the heart, which is particularly helpful to the physician. In this regard, if the patient is subject to atrial arrhythmias, it may be advantageous to specifically examine atrial IEGM data, such as the aforementioned $A_R$ TIP-can IEGM; whereas, if the patient is subject to ventricular arrhythmias, it may instead be advantageous to examine ventricular IEGM data, such as the aforementioned $V_R$ TIP-$V_L$ TIP IEGM. Lead systems often include numerous electrodes, thereby providing a wide range of choices of electrode pairs for recording IEGMs. In addition to the aforementioned $A_R$ TIP, $V_R$ TIP, $V_L$ TIP and device housing electrodes, lead systems for use with state-of-the-art devices may include: a right atrial ring electrode ($A_R$ RING), a left ventricular tip electrode ($V_L$ TIP), a left atrial ring electrode ($A_L$ RING), a left atrial coil ($A_L$ COIL), a right ventricular coil ($R_V$ COIL), a left ventricular tip electrode ($V_L$ TIP), a left ventricular ring electrode ($V_L$ RING), left ventricular coil ($V_L$ COIL). Typically, IEGMs that are sensed between the device housing and one of the electrodes implanted on or within the heart, such as between the $V_R$ TIP and the device housing, are referred to as "unipolar" IEGMs. IEGMs sensed between a pair of the electrodes both implanted on or within the heart, such as between the $V_R$ TIP and the $V_R$ RING, are referred to as "bipolar" IEGMs.

As can be appreciated, given memory and power limitations within an implantable device, it is not typically feasible to sense and record IEGM data from every possible pair or electrodes. Accordingly, physicians are invited to select particular electrode configurations for recording IEGM data of particular interest. For example, the physician may select two atrial channel IEGMs (i.e. IEGMs derived primarily from atrial electrodes) and two ventricular channel IEGMs (i.e. IEGMs derived primarily from ventricular electrodes) for recording. Moreover, it is not ordinarily feasible to record each of the selected IEGMs at all times. Rather it is typically feasible only to record IEGMs and corresponding event markers during periods of interest, such as during an arrhythmia. Accordingly, state-of-the-art devices are configured to record the selected IEGM data only in response to the detection of arrhythmias or other anomalous events of interest (PACs, PVCs, etc.), or following an automatic mode switch (AMS) from one pacing mode to another. The events triggering the recording of IEGMs are referred to as "triggers." In state-of-the-art devices, the physician is invited to select the particular triggers to be used by the device in activating the recording of the IEGM data. With current state-of-the-art devices, once any particular selected trigger is detected by the device, each of the selected IEGMs is then sensed and recorded along with the event records containing corresponding event makers.

In many cases, it is also desirable to record IEGM data prior to the trigger, as well as just following the trigger, so that the physician can review the conditions leading up to the trigger. This is particularly important insofar as arrhythmias are concerned as the physician usually wants to be able to review IEGM data prior to the onset of the arrhythmia so as to more readily diagnosis the cause of the arrhythmia. Accordingly, many state-of-the-art devices are configured to allow so-called "pre-trigger IEGMs" to be saved along with IEGMs recorded during an arrhythmia. Briefly, the device continuously detects and records IEGMs in a circular first-in/first-out (FIFO) queue. If an arrhythmia is detected, the IEGMs recorded just prior to the onset of the arrhythmia are transferred from the FIFO queue to long-term memory, so that the pre-trigger IEGMs can be saved along with IEGMs recorded during the arrhythmia itself for subsequent review by the physician. In this manner, IEGMs detected during the period of time leading to the onset of the arrhythmia is saved in long-term memory for subsequent review by the physician, without requiring all IEGMs to be saved in long-term memory at all times. Pre-trigger IEGMs can also be transferred to long-term memory upon detection of other selected triggers, such as pacemaker mediated tachycardias (PMTs), PVCs, AMS events, etc. A particularly effective technique for implementing pre-trigger memory is set forth in U.S. patent application Ser. No. 10/782,684, of Kroll, filed Feb. 18, 2004, entitled "System and Method for Controlling the Recording of Diagnostic Medical Data in an Implantable Medical Device."

Thus, state-of-the-art devices provide for the recording of pre-trigger and post-trigger IEGMs upon detection of particular diagnostic triggers chosen by the physician or other clinician. Moreover, the physician or other clinician can also specify the particular IEGM "views," i.e. the particular electrode pairs for use in sensing the IEGMs to be recorded. This provides considerable flexibility to the physician in obtaining IEGMs of interest while also reducing the amount of data the device itself needs to record. However, room for improvement remains. As noted, upon detection of any of the selected triggers, the device records each of the selected IEGMs. In many cases, though, the physician may be interested only in particular IEGMs upon detection of particular triggers. Accordingly, it would be desirable to provide for trigger-specific recording of cardiac signal data, i.e., it would be desirable to provide implantable medical devices that are capable of sensing and recording different IEGMs in response to different triggers. It is to this end that the invention is primarily directed.

SUMMARY OF THE INVENTION

In an exemplary embodiment, a method is provided for use by an implantable medical device such as a pacemaker for controlling the recording of signals by the device, wherein the device is capable of recording different types of signals in response to different diagnostic triggers. The method comprises: storing an indication of particular signals (such as IEGMs) to be stored in response to particular diagnostic triggers; sensing signals within the patient; detecting the occurrence of a particular trigger within the patient; identifying, based on the trigger, the particular signals to be stored in response to the trigger; and then storing the particular signals identified for storage. In an illustrative example, the signals to be stored are cardiac signals such as IEGMs. The indication of the particular IEGMs or other cardiac signals to be stored is preferably initially provided by a physician or other clinician via an external programmer. In this manner, the physician can select different IEGMs to be stored in response to different diagnostic triggers, thereby providing greater diagnostic flexibility to the physician while reducing the amount of IEGM data the device itself must record, at least as compared to those devices that record all selected IEGMs in response to the occurrence of any selected triggers.

In one example, the physician also initially selects the particular diagnostic triggers to be used via the external programmer. Examples include: an AMS detection trigger; a PMT trigger; an AT trigger, an AF trigger, a VT trigger, a VF trigger and a consecutive PVC trigger (i.e. two or more PVCs occurring in sequence). The physician also selects the particular IEGMs to be stored for each selected trigger. IEGMs are selected by specifying different electrode combinations from among the electrodes available to the device, such as $A_R$ TIP, $A_R$ RING, $V_L$ TIP, $A_L$ RING, $A_L$ COIL, $V_R$ TIP, $V_R$ RING, $R_V$ COIL, $V_L$ TIP, $V_L$ RING, $V_L$ COIL and device housing electrodes, as well as shorted combinations of the electrodes (wherein two or more individual electrodes are employed as a single combined electrode). Then, during use, whenever a particular one of the selected triggers is detected, the implantable device records only those IEGMs that had been selected for that particular trigger. The IEGMs are eventually transmitted to the external programmer for display thereon. In this manner, the physician can conveniently review the particular IEGMs of interest for a given trigger. Moreover, the implantable device need only record the particular IEGMs of interest for a particular trigger, rather than all selected IEGMs, thus saving considerable storage space.

In general, any number of triggers can be selected by a physician to trigger the recording of IEGMs or other diagnostic data, and any number of IEGMs can be selected for use with each trigger, allowing considerable flexibility. In practice, to limit the amount of IEGM data that needs to be stored within the implantable device, the device may be configured to permit only a few IEGMs to be specified for each trigger. For example, the device may be equipped to store only two or three IEGMs for each detected trigger. The particular IEGMs to be recorded may, of course, differ depending upon the particular trigger that is detected. As can be appreciated, a wide variety of implementations can be exploited, wherein various limitations are imposed either on the choice of IEGMs, the choice of triggers, or both, so as to reduce the amount of data that needs to be stored within the device itself. Preferably, a FIFO memory is employed so that, if previously recorded IEGM data needs to be erased to accommodate newly recorded data, the oldest data is overwritten while more recently recorded data is preserved.

In one specific example, the device is equipped to sense a total of four IEGMs at once—two atrial and two ventricular—but is only configured to record a total of three IEGMs in response to a given trigger. In that implementation, the physician specifies primary and secondary atrial channels and primary and secondary ventricular channels for use in sensing IEGMs. For example, for the atrial channels, the physician may select an atrial unipolar IEGM as the primary channel and an atrial bipolar IEGM as the secondary channel. Likewise, for the ventricular channels, the physician may select a ventricular unipolar IEGM as the primary channel and a ventricular bipolar IEGM as the secondary channel. The various triggers are classified as either atrial-related triggers or ventricular-related triggers. The atrial-related triggers include, e.g., the AMS detection trigger; the PMT trigger; the AT trigger, and the AF trigger. The ventricular-related triggers include, e.g., the VT trigger, the VF trigger and the consecutive PVC trigger.

Whenever an atrial-related trigger is detected, both atrial channel IEGMs are recorded, whereas only the primary ventricular channel IEGM is recorded. In contrast, whenever a ventricular-related trigger is detected, both ventricular channel IEGMs are recorded, whereas only the primary atrial channel IEGM is recorded. Thus, atrial arrhythmias and other anomalous atrial events, such as PMTs, trigger the recording of two atrial IEGMs and one ventricular IEGM; whereas ventricular arrhythmias and other anomalous ventricular events, such as consecutive PVCs, trigger the recording of two ventricular IEGMs and one atrial IEGM. In this manner, the physician is provided with a total of three IEGMs in response to each trigger event, with the particular IEGMs automatically selected based on the chambers in which the event occurred. The device saves memory resources by recording only three of the four sensed IEGM channels.

As can be appreciated, other arrangements can be employed. For example, an implantable device may be provided that is capable of sensing only two IEGMs at once—one atrial and one ventricular—but is capable of recording only one IEGM. In that implementation, whenever an atrial-related trigger is detected, the single atrial channel IEGM is recorded. In contrast, whenever a ventricular-related trigger is detected, the single ventricular channel IEGM is recorded. In general, any arbitrary number of channels can be sensed and any arbitrary number of channels can be recorded, limited only by the capabilities of the device. Moreover, the triggers can be further classified based on the left and right chambers. That is, certain atrial triggers might be classified as being left atrial-triggers or right atrial-triggers; whereas certain ventricular triggers might be classified as being left ventricular-triggers or right ventricular-triggers. Examples include an idiopathic RV tachycardia-trigger and an idiopathic LV tachycardia-trigger. Particular IEGMs are then automatically selected for storage that emphasize the particular left or right chamber depending upon the trigger, such as a left ventricular unipolar IEGM (i.e. LV-IEGM) recorded in response to idiopathic LV tachycardia or a right chamber unipolar IEGM (i.e. an RV-IEGM) recorded in response to idiopathic RV tachycardia.

Preferably, the implantable device is equipped to also store pre-trigger IEGM. That is, upon detection of a particular trigger, the device moves IEGMs stored by the device just prior to the trigger into long-term memory for storage along with IEGMs recorded during or immediately after the triggering event. In one example, the device automatically records all IEGMs that are being sensed within the temporary pre-trigger memory. Then, upon detection of a trigger, the device transfers into long-term memory only that portion of the pre-trigger memory corresponding to the IEGMs to be stored for that trigger. For example, in the implementation where the device is equipped to sense four IEGM channels but store only three IEGM channels in response to a trigger, the device temporarily records all four IEGMs in the pre-trigger memory, but transfers only three of the channels of IEGMs into long-term memory upon detection of a trigger. The three channels that are transferred depend on whether the trigger is atrial-related or ventricular-related.

In some examples, in addition to recording IEGMs, the device records event records or other appropriate diagnostics data. The particular event records to be stored as part of the IEGM data can also depend on the particular trigger. That is, atrial-related event records can be stored in response to atrial-related triggers; whereas ventricular-related event records can be stored in response to ventricular-related triggers.

Moreover, in some examples, in addition to using triggers that are derived from IEGMs, the device also exploits triggers detected within other signals, such as within signals provided by blood pressure sensors, blood oxygen saturation sensors or the like. For example, upon detection of a sudden, significant drop in blood pressure, the device records IEGM data as well as blood pressure data for subsequent physician review.

In an another exemplary embodiment, a method is provided for use by an external system (such as an external programmer) for controlling the display of signals recorded by an implantable medical device capable of recording different signals within a patient in response to different diagnostic triggers detected within the patient. During an initial programming session, the external system receives user selections of particular signals to be recorded by the implantable medical device in response to particular diagnostic triggers detected within the patient. The user selections generally specify different signals to be recorded in response to different diagnostic triggers. The user selections are transmitted to the implantable medical device for storage therein. During a subsequent follow-up session, which may be weeks or months later, the external system then receives a plurality of trigger-specific signals that had been recorded by the implantable medical device in response to different triggers detected within the patient. The external system displays the trigger-specific signals along with an indication of the corresponding triggers. In an illustrative example, the signals to be stored are cardiac signals such as IEGMs. In this manner, a physician or other user of the external system can conveniently program the implantable device to record different IEGMs in response to different diagnostic triggers, thereby providing greater diagnostic flexibility to the physician.

As can be appreciated, a wide variety of techniques may be implemented in accordance with the principles of the invention and the foregoing embodiments are merely illustrative.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description includes the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Overview of Implantable Medical System

Figure 1:
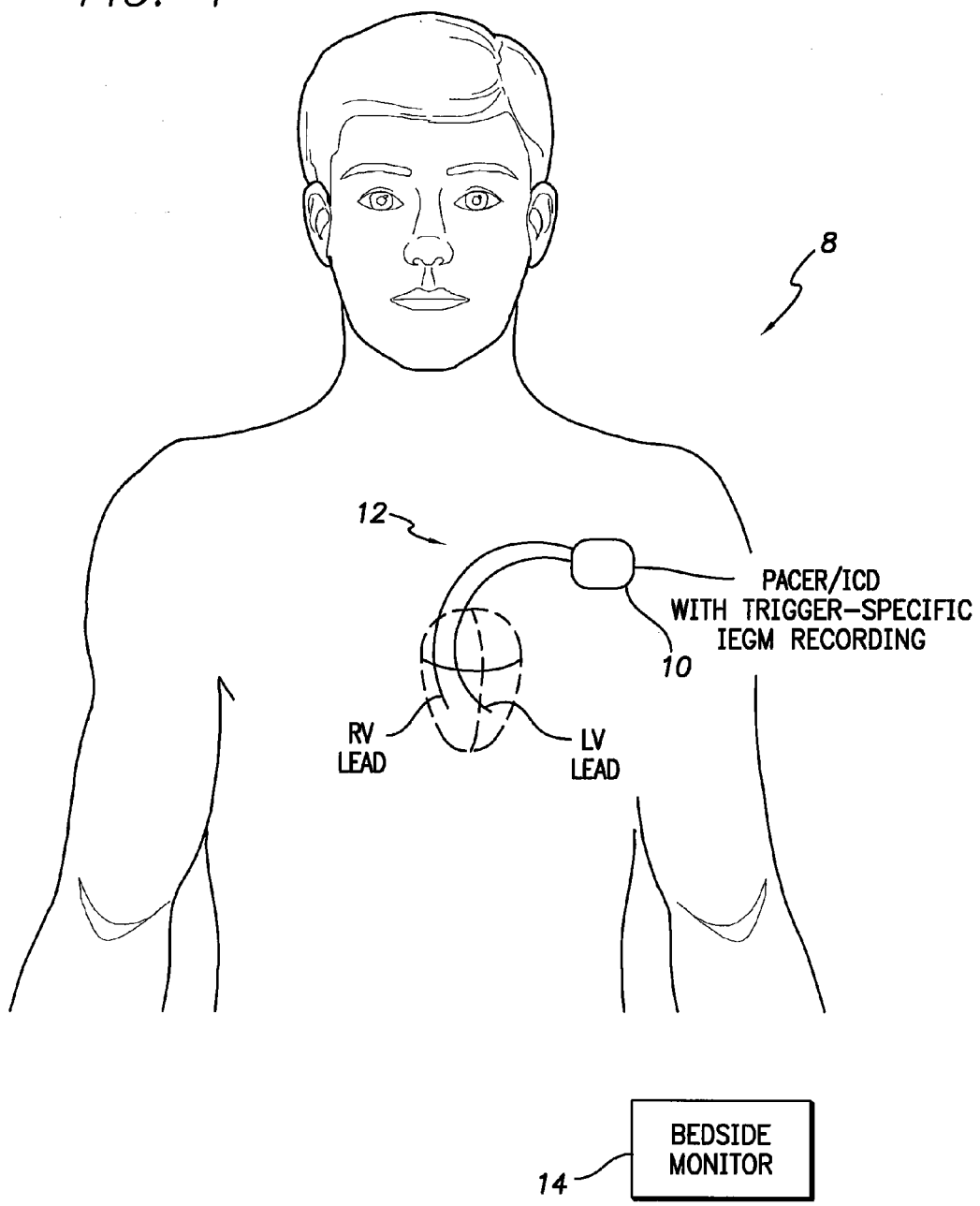
FIG. 1 illustrates pertinent components of an implantable medical system having a pacer/ICD equipped to perform trigger-specific IEGM recording.
Figure 9:
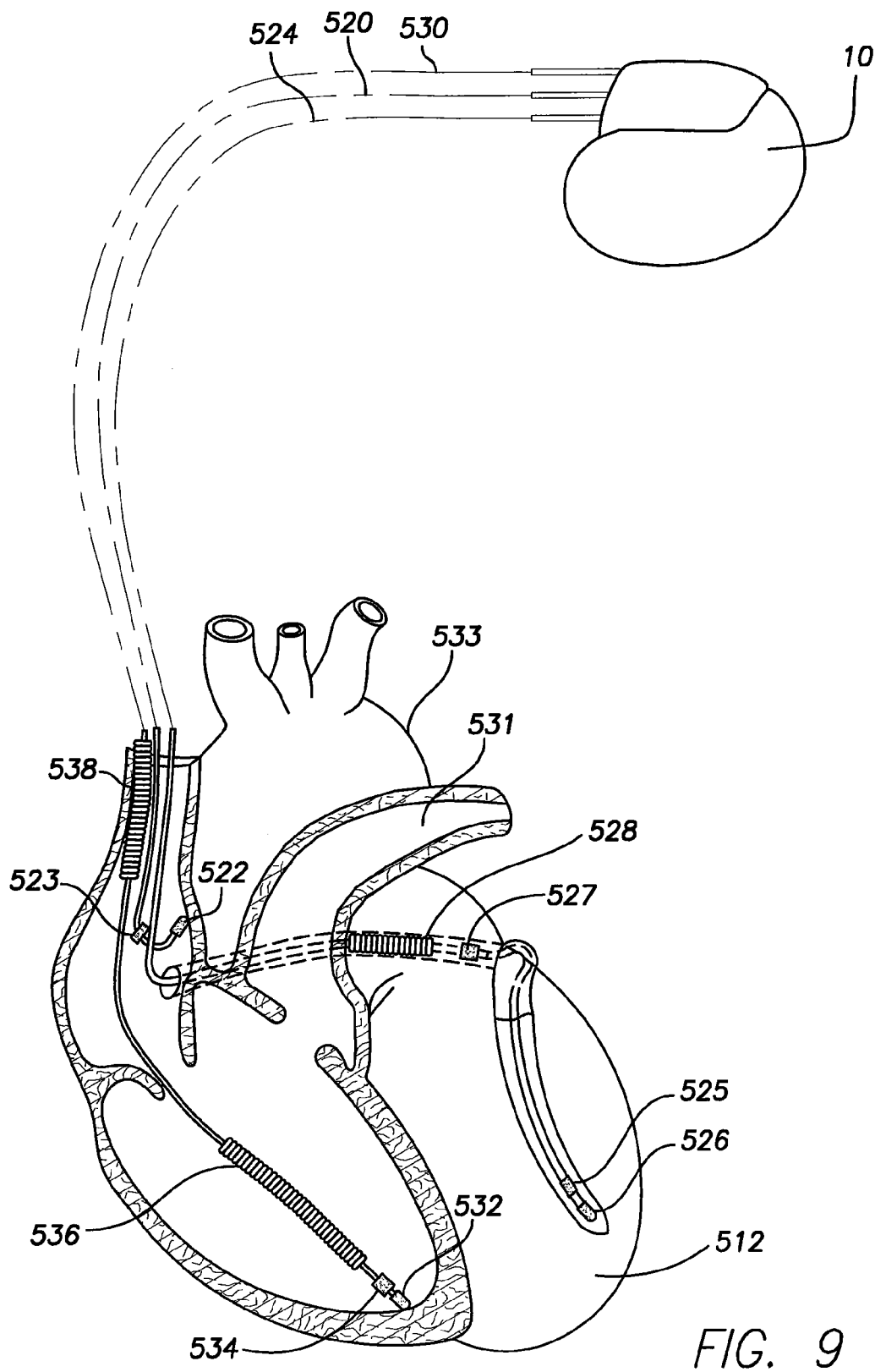
FIG. 9 is a simplified diagram illustrating the pacer/ICD of FIG. 1 in electrical communication with three leads implanted into the heart of a patient for delivering multi-chamber stimulation and shock therapy.

FIG. 1 illustrates an implantable medical system 8 having a pacer/ICD 10 equipped to perform trigger-specific recording of IEGM data, i.e. the pacer/ICD is capable of sensing and recording particular IEGMs in response to particular triggers. To this end, during an initial programming session, the pacer/ICD receives and stores a set of user selections—initially input through an external programmer device (FIG. 11)—of particular IEGMs to be sensed and stored in response to particular triggers detected within the patient. During use, the pacer/ICD 10 receives voltage signals from various cardiac pacing leads 12 (only two of which are shown in the FIG. 1) from which various channels of IEGMs are derived including, for example, a unipolar $A_R$ TIP-can IEGM and a bipolar $V_R$ TIP-$V_L$ TIP IEGM. A more complete set of exemplary pacing leads is shown in FIG. 9, discussed below. The pacer/ICD analyzes the IEGMs sensed using the leads to detect the occurrence of the selected triggers and, in response, the pacer/ICD stores the particular IEGMs that had been selected by the user for storage in response to those triggers.

The stored IEGMs, along with other appropriate diagnostic information, may be transmitted to a bedside monitor 14, if one is provided, for forwarding to a physician or other clinician for immediate review. The bedside monitor may be directly networked with a centralized computing system, such as the HouseCall™ system of St. Jude Medical, for promptly notifying the physician of any abnormal conditions, particularly any life-threatening ventricular tachyarrhythmias. Networking techniques for use with implantable medical systems are set forth, for example, in U.S. Pat. No. 6,249,705 to Snell, entitled "Distributed Network System for Use with Implantable Medical Devices." Additionally or alternatively, the stored IEGMs may be transmitted to the external programmer (FIG. 11) for review during a follow-up session with the patient. The physician may then adjust the operation of the pacer/ICD to activate, deactivate or otherwise control any therapies that are automatically applied by the pacer/ICD. The physician may also reprogram the pacer/ICD to sense and store different sets of IEGMs in response to the same, or different, sets of triggers.

Figure 2:
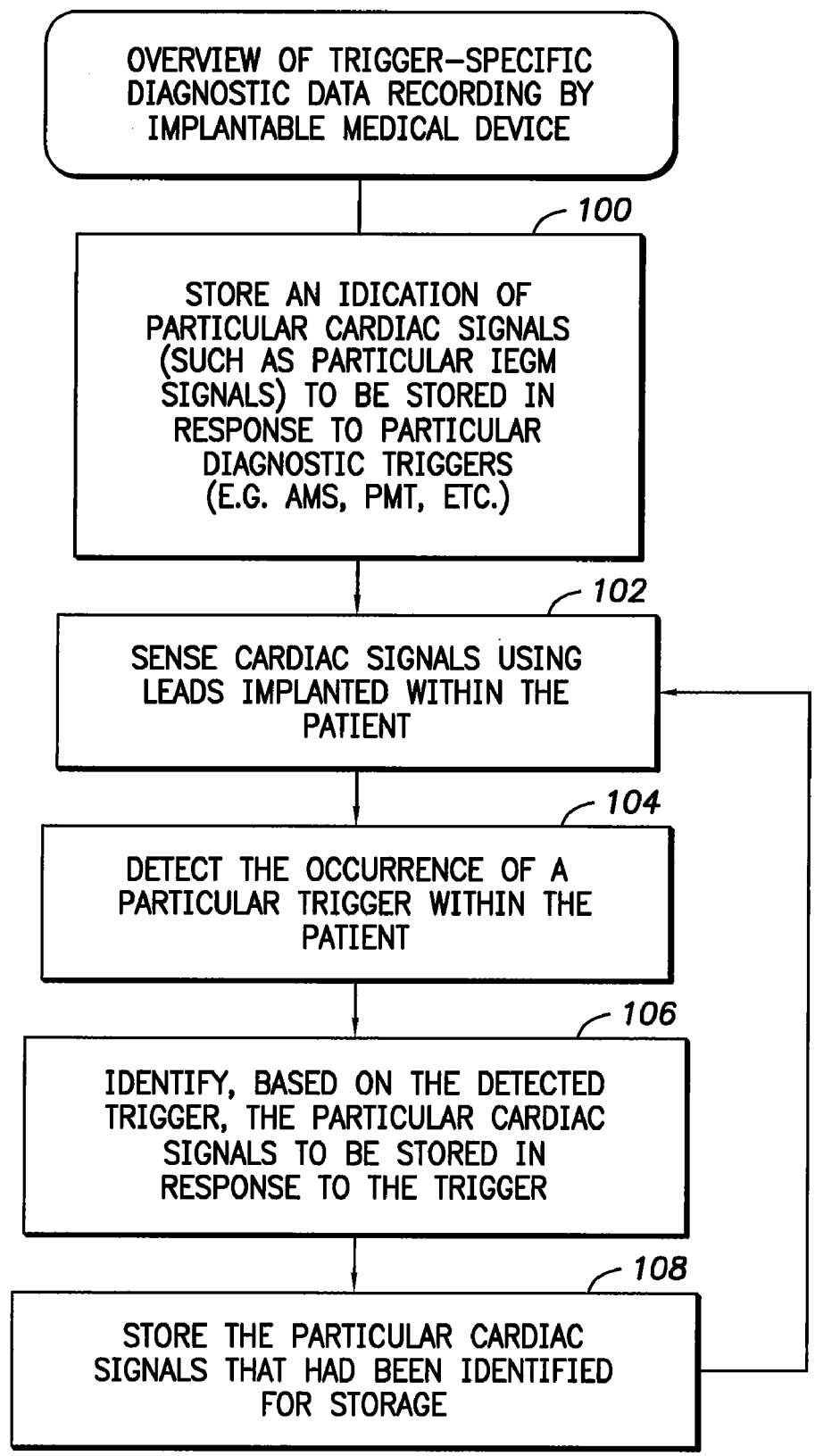
FIG. 2 is a flow chart summarizing the trigger-specific IEGM recording techniques of the pacer/ICD of FIG. 1.

FIG. 2 summarizes the techniques performed by the pacer/ICD for providing trigger-specific recording of IEGM data or other diagnostic data. At step 100, the pacer/ICD stores an indication of particular cardiac signals (such as particular IEGM signals) to be stored in response to particular diagnostic triggers (e.g. AMS, PMT, etc.) The indication of particular cardiac signals to be stored in response to particular diagnostic triggers is typically derived from programming signals received from an external programmer based on selections or inputs provided by a physician or clinician. At step 102, the pacer/ICD senses cardiac signals using leads implanted within the patient. At step 104, the pacer/ICD detects the occurrence of a particular trigger within the patient and, at step 106, identifies, based on the detected trigger, the particular cardiac signals to be stored in response to the trigger. At step 108, the pacer/ICD stores the particular cardiac signals identified for storage, i.e. the pacer/ICD records the particular cardiac signals that had been originally selected by the physician for storage in response to particular diagnostic triggers Thus, FIGS. 1 and 2 provide an overview of an implantable system and method for performing trigger-specific recording of IEGM data. Although a pacer/ICD is illustrated, it should be understood that the techniques of the invention may be implemented within other implantable medical devices.

Generalized Example of Trigger-Specific IEGM Recording Techniques

Figure 3:
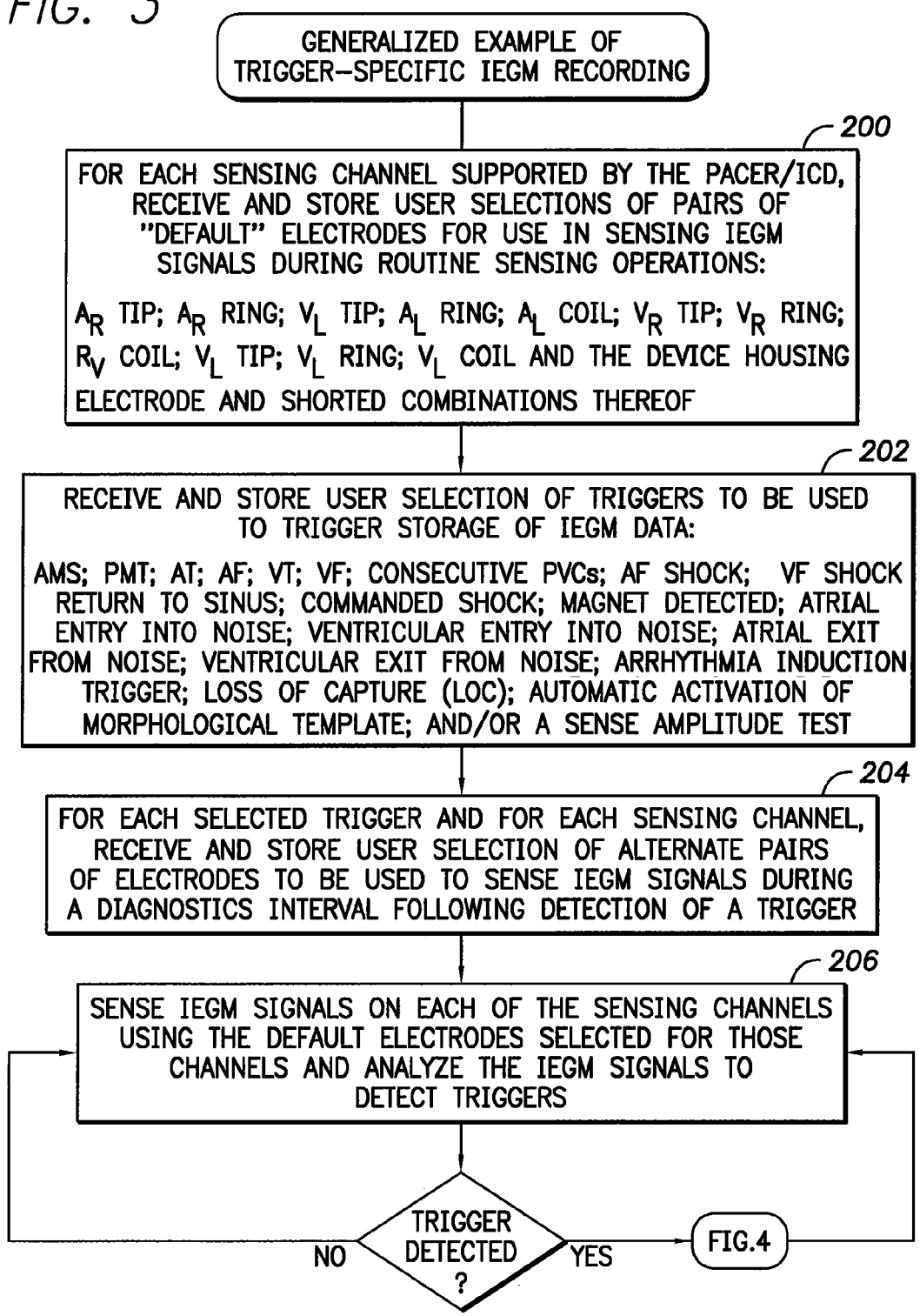
FIG. 3 is a flow chart providing a generalized example of the trigger-specific IEGM recording techniques of FIG. 2.
Figure 4:
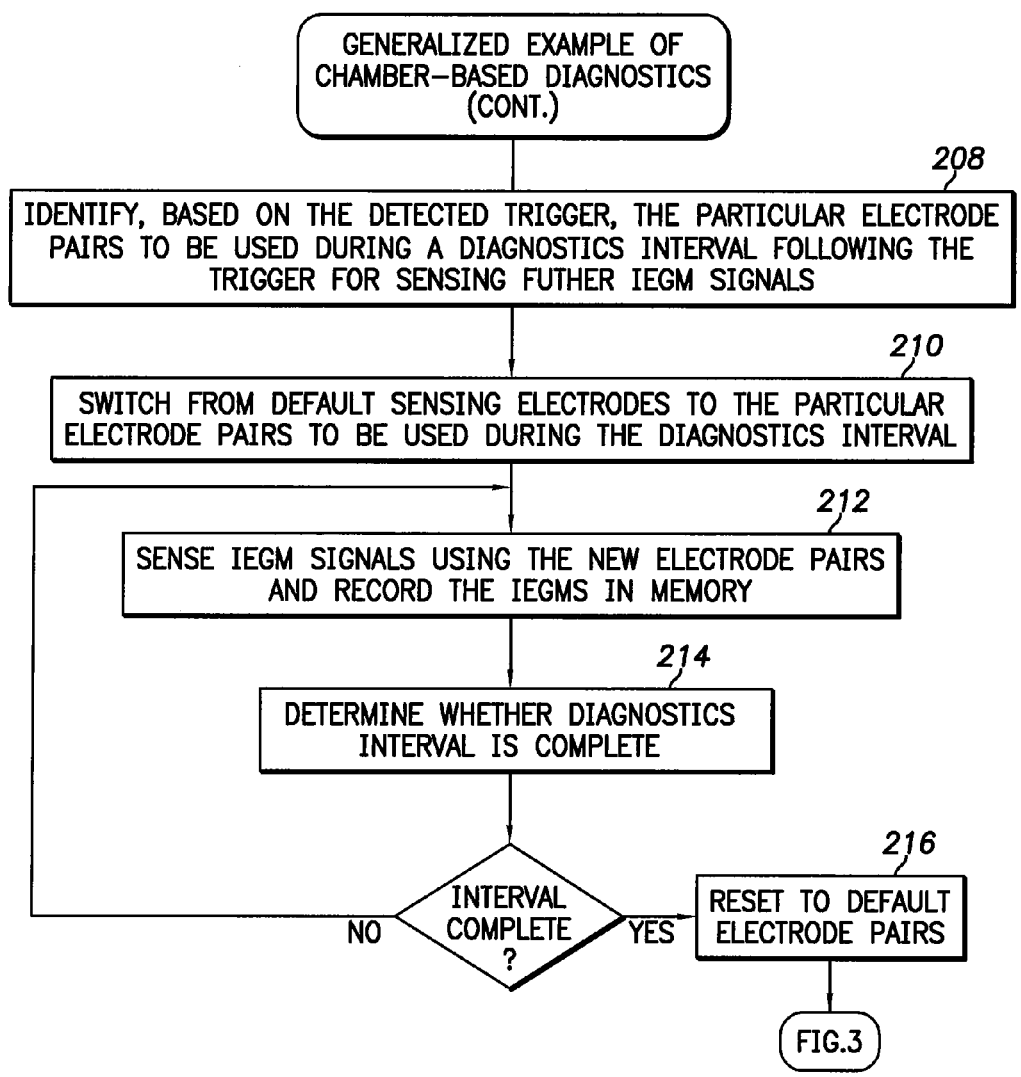
FIG. 4 is a flow chart illustrating post-trigger recording steps for use with the example of FIG. 3.

FIGS. 3 and 4 provide a generalized example of the trigger-specific IEGM recording techniques of FIG. 2. At step 200, for each sensing channel supported by the implantable medical system, the pacer/ICD receives and stores a use selection of pairs of "default" electrodes for use in sensing IEGM signals during routine sensing operations. For example, if four sensing channels are provided within the pacer/ICD, the pacer/ICD receives and stores an identification of four pairs of electrodes for use in routine sensing operations. The user selection is initially provided by a physician or other clinician via an external programmer, and then relayed to the pacer/ICD for storage within computer memory therein. The choice of electrodes depends upon the particular set of leads implanted in the patient. In one example, the leads provide each of the following electrodes: $A_R$ TIP; $A_R$ RING; $V_L$ TIP; $A_L$ RING; $A_L$ COIL; $V_R$ TIP; $V_R$ RING; $R_V$ COIL; $V_L$ TIP; $V_L$ RING; $V_L$ COIL and the device housing (can). In general, any combination of electrodes can be selected as an electrode sensing pair for sensing IEGM signals on one of the sensing channels. Also, two or more electrodes can be shorted together to provide a single combined electrode for use in combination with other electrodes to form an electrode "pair." For example, the $A_R$ TIP and $A_R$ RING electrodes can be shorted to form a single "electrode" for use in combination with the device housing to sense IEGMs. Preferably, the pairs of electrodes (or combinations of electrodes) are carefully chosen by the user so as to permit the device to efficiently and reliably perform routine sensing operations for use detecting arrhythmias and for controlling pacing in response thereto. See, for example, U.S. Pat. No. 5,707,398 to Lu, entitled "Automatic Determination of Optimum Electrode Configuration for a Cardiac Stimulator." Note that, in some examples, all possible electrode pairs are regarded as "default" pairs, i.e. the pacer/ICD is equipped to accommodate a sufficient number of sensing channels to sense IEGMs using all possible pairs of electrodes, so that a separate designation of default electrodes is not required.

At step 202, the pacer/ICD receives and stores a user selection of triggers to be used to trigger storage of IEGMs and other diagnostic data. The choice of triggers depends upon the capabilities of the device. In a typical example, the pacer/ICD is at least capable of detecting PMT, AF, AT, VT, VF and consecutive PVCs and so corresponding triggers can be selected by the user. A particularly effective technique for detecting PMT is set forth in U.S. Pat. No. 5,074,308, to Sholder, et al., entitled "System And Method For Recognizing Pacemaker-Mediated Tachycardia." Other triggers that might be exploited include: an AF Shock trigger (indicating whether an AF cardioversion shock has been delivered to the patient); a VF Shock trigger (indicating whether an VF defibrillation shock has been delivered to the patient); a Return to Sinus trigger (indicating whether the patient's heart has reverted to a sinus rhythm following some non-sinus rhythm such as an atrial or ventricular arrhythmia); a Commanded Shock trigger (indicating whether the pacer/ICD has been controlled by an external device to deliver a shock to the patient, as may be performed by a physician following device implant so as to test the device); a Magnet trigger (indicating whether a magnet has been positioned near the pacer/ICD, as may be required during programming of the device); an Atrial Entry Into Noise trigger (indicating that the pacer/ICD is detecting significant amounts of noise on its atrial channels); a Ventricular Entry Into Noise trigger (indicating that the pacer/ICD is detecting significant amounts of noise on its ventricular channels); an Atrial Exit From Noise trigger (indicating that the pacer/ICD is no longer detecting significant amounts of noise on its atrial channels); a Ventricular Exit From Noise trigger (indicating that the pacer/ICD is no longer detecting significant amounts of noise on its ventricular channels); an Arrhythmia Induction trigger (indicating that the pacer/ICD was controlled by an external device to cause an arrhythmia to occur within the patient, as may be performed by a physician following device implant so as to test the device); a Loss Of Capture (LOC) trigger (indicting that a LOC occurred, i.e. the pacer/ICD detected that pacing pulses were not being properly captured within the heart of the patient); an Automatic Activation of Morphological Template trigger (indicating that the pacer/ICD has accessed a previously stored morphology template) and a Sense Amplitude Test trigger (indicating that the pacer/ICD has performed a sense amplitude test, which is typically performed about once a day). Still other triggers that might be exploited include any of a variety of device maintenance triggers associated with device maintenance functions, such as capacitor reformation and the like.

If the pacer/ICD is equipped to perform AMS, an AMS trigger can also be selected. With AMS, the pacer/ICD reverts from a tracking mode such as a VDD or DDD mode to a nontracking mode such as VVI or DDI mode upon detection of certain conditions, particularly AT/AF. VDD, DDD, VVI and DDI are standard device codes that identify the mode of operation of the device. DDD indicates a device that senses and paces in both the atria and the ventricles and is capable of both triggering and inhibiting functions based upon events sensed in the atria and the ventricles. VDD indicates a device that sensed in both the atria and ventricles but only paces in the ventricles. A sensed event on the atrial channel triggers ventricular outputs after a programmable delay, the pacemaker's equivalent of a PR interval. VVI indicates that the device is capable of pacing and sensing only in the ventricles and is only capable of inhibiting the functions based upon events sensed in the ventricles. DDI is identical to DDD except that the device is only capable of inhibiting functions based upon sensed events, rather than initiating or activating functions. As such, the DDI mode is a non-tracking mode precluding it from activating ventricular outputs in response to sensed atrial events.

Other cardiac signal-based triggers may be specified based on the detection capabilities of the device. For example, if the pacer/ICD is capable of detecting, e.g., atrial flutter, supraventricular tachycardia (SVT), sinus tachycardia (ST), atrioventricular re-entrant tachycardia (AVRT), atrioventricular nodal re-entrant tachycardia (AVNRT), idiopathic RV tachycardia, idiopathic LV tachycardia, and/or atrial or ventricular bigeminy, trigeminy, quadrigeminy, etc., then corresponding triggers can be selected. In general, any event (or combination of events) detectable by the pacer/ICD within the electrical cardiac signals of the heart can be employed as a trigger, whether the event constitutes an arrhythmia or otherwise.

Moreover, if the device is equipped with one or more sensors, then various non-cardiac signal-based triggers can be specified as well. Exemplary sensors include: a blood oxygen sensor, a pH sensor, a temperature sensor, a blood glucose sensor, an accelerometer, a cardiac output sensor, a contractility sensor, an acoustic sensor and a pressure sensor. In general, any detectable event within the signals provided by the sensors can be used as a trigger for the purposes of triggering the recording of IEGM data. As just one example, blood pressure and/or contractibility signals can be analyzed to detect vasovagal syncope, which in turn triggers the storage of IEGM data during, and potentially before, the episode of syncope. Vasovagal syncope detection techniques are discussed, e.g., in U.S. Pat. No. 6,647,295 to Florio, et al., entitled "Implantable Cardiac Stimulation Device with Detection and Therapy for Patients with Vasovagal Syncope." In some examples, in addition to storing IEGM data in response to a sensor-based trigger, the pacer/ICD is programmed to also store data from the sensor that triggered the storage of the IEGM data.

At step 204, for each selected trigger and for each sensing channel, the pacer/ICD receives and stores a user selection of alternate pairs of electrodes to be used to sense IEGM signals during a diagnostics interval following detection of a trigger. That is, during routine sensing, the pacer/ICD uses the default electrode pairs specified at step 200. However, once an event such as an arrhythmia is detected that triggers the recording of IEGM data, the device can be programmed to switch to an alternate set of electrode pairs so as to record IEGMs of particular interest during that particular event. In an example where there are four total sensing channels, the user may specify, e.g., that three of the four default sensing channels be switched during AT to sensing IEGMs using pairs of atrial electrodes, while only one continues to sense using a default pair of ventricular electrodes, so as to primarily record IEGMs that emphasize atrial cardiac signals during AT. Note, also, that in the preferred embodiments the storage of IEGMs includes the storage of event markers, i.e. "IEGM data" is recorded as generally defined above. Hence, whenever IEGMs are stored, corresponding event markers are stored as well. In other embodiments, the storage of event markers can be performed independently of IEGMs.

Table I provides a four channel example wherein the following electrodes are available: $A_R$ TIP; $A_R$ RING; $V_L$ TIP; $A_L$ RING; $A_L$ COIL; $V_R$ TIP; $V_R$ RING; $R_V$ COIL; $V_L$ TIP; $V_L$ RING; $V_L$ COIL and the can; and wherein the following triggers have been selected: PMT, AF, AT, VT, VF and consecutive PVCs. In general, though, any combination of electrode sensing pairs (including pairs with shorted electrodes) may be selected for use with any selected trigger, depending upon the capabilities of the pacer/ICD and the electrodes provided with the leads.

TABLE I

| TRIGGER | SELECTED ELECTRODE PAIRS |
| --- | --- |
| PMT | $A_R$ TIP-$A_R$ RING |
|  | $V_L$ TIP-CAN |
|  | $A_L$ RING-CAN |
| AF | $A_R$ TIP-$A_R$ RING |
|  | $V_L$ TIP-CAN |
|  | $A_L$ RING-CAN |
|  | $A_R$ TIP-$V_R$ TIP |
| AT | $A_R$ TIP-$A_R$ RING |

TABLE I-continued

| TRIGGER | SELECTED ELECTRODE PAIRS |
|---|---|
| VT | $V_L$ TIP-CAN<br>$A_L$ RING-CAN<br>$A_R$ RING-$V_R$ RING<br>$V_R$ TIP-$V_R$ RING<br>$A_R$ TIP-CAN; |
| VF | $V_L$ RING-CAN<br>$V_R$ COIL-$A_R$ COIL<br>$V_R$ TIP-$V_R$ RING<br>$A_R$ TIP-CAN; |
| CONSECUTIVE PVCs | $V_L$ RING-CAN<br>$V_R$ COIL-$A_R$ COIL<br>$V_R$ TIP-$V_R$ RING<br>$A_R$ TIP-CAN |

Then, beginning at step 206, the pacer/ICD senses IEGM signals on each of the sensing channels using the default electrodes selected at step 200 for those channels and analyzes the IEGM signals to detect any triggers. Assuming no triggers are detected, step 206 is simply repeated so as to sense and analyze additional IEGM signals. However, once a trigger is detected, processing continues at step 208 of FIG. 4 where the pacer/ICD identifies, based on the detected trigger, the particular electrode pairs to be used during a "diagnostics interval" following the trigger for sensing further IEGM signals to be stored for diagnostics purposes. That is, the pacer/ICD examines information previously stored within its memory (at step 204) to read out the electrode pairs to be activated in response to the trigger. Again, see Table I. The predetermined diagnostics interval specifies how long the pacer/ICD will record IEGMs in response to a trigger. The interval may vary depending upon the particular trigger. For some triggers, such as consecutive PVCs, it may be appropriate for the user to specify a predetermined duration for the diagnostics interval during a programming session at the same time the triggers themselves are selected. With other triggers, particularly arrhythmia triggers, it may instead be appropriate for the pacer/ICD to record IEGMs during the entire duration of the arrhythmia, rather than to specify a fixed diagnostics interval.

For implementations using pre-trigger memory, the "diagnostics interval" actually begins before the onset of the trigger. The example of FIGS. 3 and 4 assumes that pretrigger memory is not used. The use of pretrigger memory is discussed below. In any case, at step 210, the pacer/ICD then switches from the default sensing electrodes (selected at step 200) to the particular electrode pairs identified for use during the diagnostics interval (at step 208). At step 212, the pacer/ICD begins sensing IEGM signals using the new electrode pairs (of step 210) and records the IEGMs in memory. At step 214, the pacer/ICD determines whether diagnostics interval is complete and, if not, returns to step 212 for further sensing. Once the diagnostics interval is complete, the pacer/ICD switches back to the default electrode pairs, at step 216, and then returns to step 206 of FIG. 3 for further processing using the default pairs of electrodes.

It should be understood that, while sensing and recording IEGMs during the diagnostics interval using the alternate pairs of electrodes (identified at step 208), the pacer/ICD may also deliver therapy in response to the condition that triggered the recording. In particular, if an arrhythmia triggered the diagnostic recording, therapy may be delivered during the arrhythmia. Moreover, while sensing and recording IEGMs during the diagnostics interval, the pacer/ICD also continues to monitor the cardiac signals to detect additional triggers and, in particular, to detect the onset of potentially more serious arrhythmias or other conditions. If a more serious arrhythmia is detected, appropriate therapy is, of course, delivered. Moreover, the pacer/ICD preferably switches the sensing electrodes to the electrodes selected by the user for use with that more serious arrhythmia. For example, if VF is detected during a diagnostics interval initially triggered by AF, the device preferably suspends AF therapy and initiates VF therapy and also switches to sensing electrodes appropriate for VF. Accordingly, in some implementations, it is appropriate to allow the user to specify the relative "priority" of different triggers during the programming session. In this manner, the device always records IEGMs using the sets of electrodes selected by the user for use with the highest priority (i.e. most serious) trigger. In one particular example, consecutive PVCs may be set to have the lowest priority; whereas VF is set to have the highest priority. In some implementations, the pacer/ICD may be equipped to allow for recording "overlap," i.e. the device continues to record IEGMs based on the lower priority trigger, while also then recording IEGMs based on the higher priority trigger once it is detected.

Four Channel Example of Trigger-Specific IEGM Recording Techniques

Figure 5:
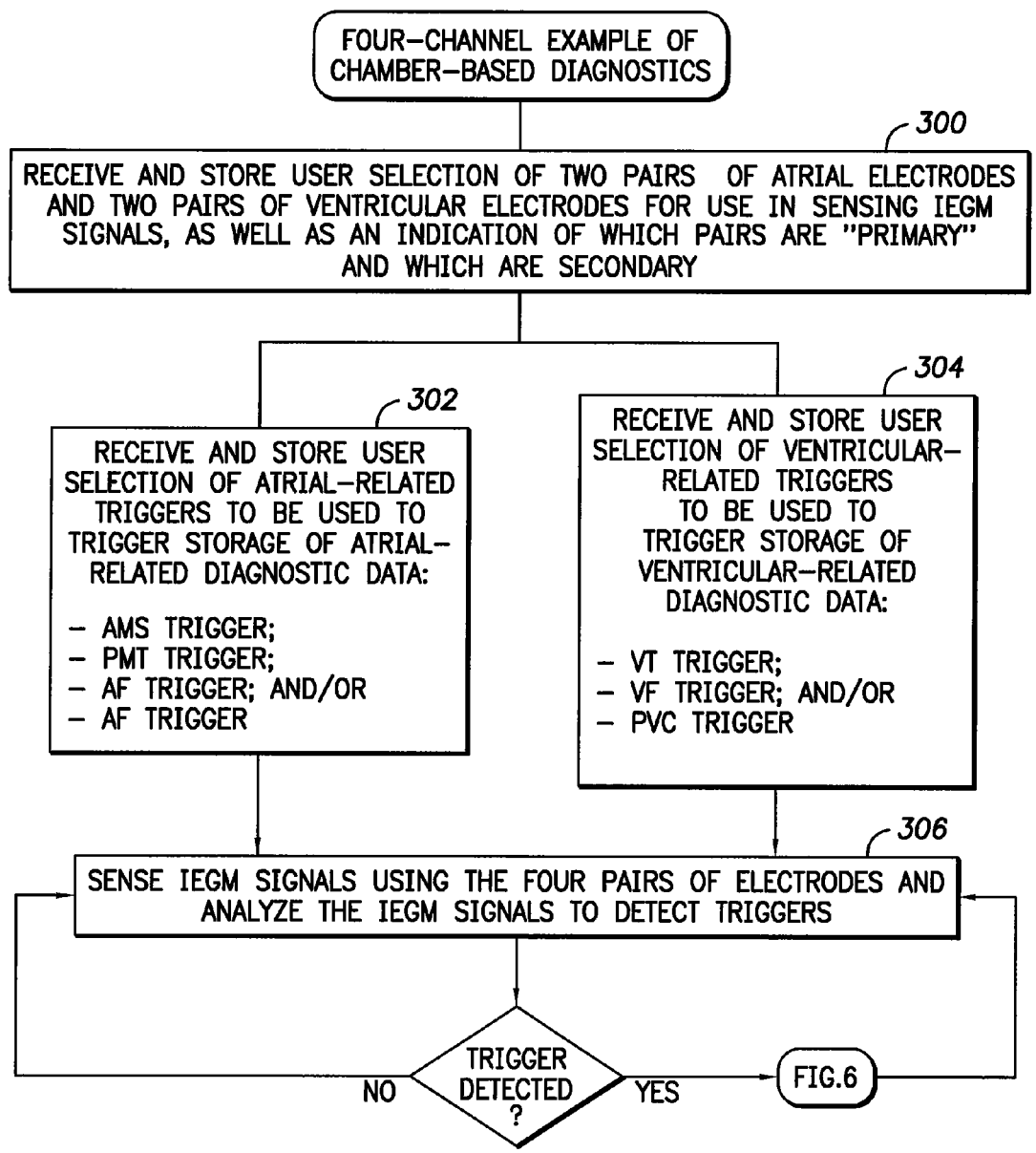
FIG. 5 is a flow chart providing a four-channel example of the trigger-specific IEGM recording techniques of FIG. 2.
Figure 6:
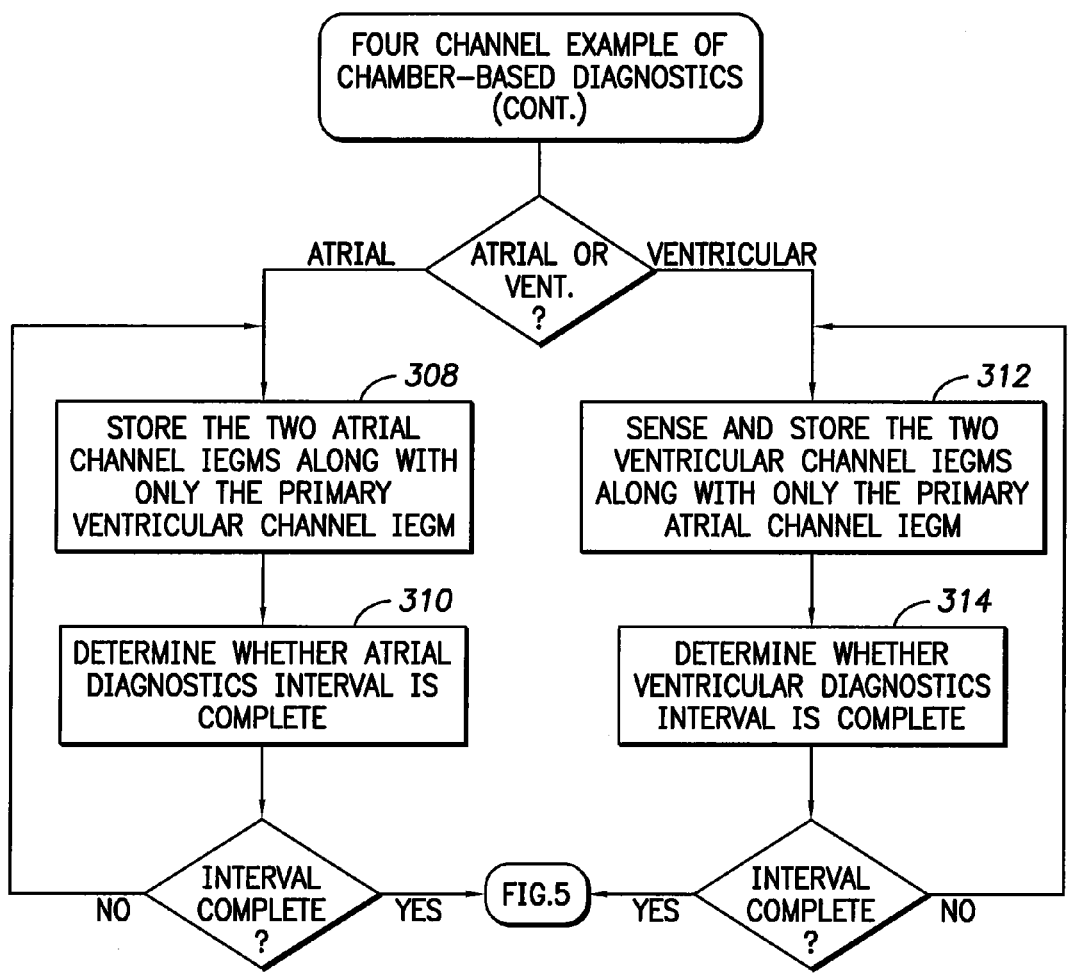
FIG. 6 is a flow chart illustrating post-trigger recording steps for use with the four-channel example of FIG. 5.

FIGS. 5 and 6 provide a four channel example of the trigger-specific IEGM recording techniques of FIG. 2, wherein triggers are classified as being atrial-based or ventricular-based. In this example, the implantable medical system supports two default atrial sensing channels and two default ventricular sensing channels. Many of the steps of FIGS. 5 and 6 are similar to those of FIGS. 3 and 4 and only pertinent differences will be described in detail. At step 300, for each of the two atrial sensing channels and for each of the two ventricular sensing channels supported by the implantable medical system, the pacer/ICD receives and stores a user selection of pairs of electrodes for use in sensing IEGM signals. That is, the pacer/ICD receives and stores an identification of two pairs of electrodes for sensing in the atria. Likewise, the pacer/ICD receives and stores an identification of two pairs of electrodes for sensing in the ventricles. Unlike the generalized example of FIGS. 3 and 4, the electrode pairs selected at step 300 are not used only during routine sensing operations. The electrode pairs are used for all sensing, including sensing during atrial or ventricular diagnostics intervals.

Additionally, at step 300, the pacer/ICD receives and stores a user selection of which pairs are "primary" and which pairs are "secondary." As will be explained, in response to atrial-related triggers, both of the atrial channels are used to record IEGMs but only the primary ventricular channel is used. Conversely, in response to ventricular-related triggers, both of the ventricular channels are used to record IEGMs but only the primary atrial channel is used.

In one specific example, the following four electrodes pairs are selected at step 300 for sensing:

Primary Atrial: $A_R$ TIP-$A_R$ RING;
Secondary Atrial: $A_L$ RING-CAN;
Primary Ventricular: $V_R$ TIP-$V_R$ RING; and
Secondary Ventricular: $V_L$ TIP-CAN Thus, in that example, in response to an atrial trigger, the pacer/ICD will record IEGM signals from the following three electrode pairs: $A_R$ TIP-$A_R$ RING; $A_L$ RING-CAN; and $V_R$ TIP-$V_R$ RING. Conversely, in response to a ventricular trigger, the pacer/ICD will record IEGM signals from the following three electrode pairs: $V_R$ TIP-$V_R$ RING, $V_L$ TIP-CAN and $A_R$ TIP-$A_R$ RING.

At step 302, the pacer/ICD receives and stores a user selection of atrial-based triggers to be used to trigger storage of IEGMs and other diagnostic data during an atrial diagnostics interval. Again, the choice of atrial-related triggers depends upon the capabilities of the device. In a typical example, the pacer/ICD is at least capable of detecting PMT, AF, AT, and performing AMS and so corresponding triggers can be selected by the user. Other atrial-related triggers may be specified based on the detection capabilities of the device. For example, if the pacer/ICD is capable of detecting, e.g., atrial flutter and/or atrial bigeminy, trigeminy, quadrigeminy, etc., then corresponding atrial-related triggers can be selected. In general, any atrial-based event detectable by the pacer/ICD within the electrical cardiac signals of the heart can be employed as an atrial-related trigger, whether the event constitutes an atrial arrhythmia or otherwise. Moreover, if the device is equipped with one or more atrial-based physiological sensors, then various non-cardiac signal-based atrial triggers can be specified as well. Exemplary sensors that might be implanted on or in the atria include: an atrial blood oxygen sensor, an atrial pH sensor, an atrial temperature sensor, an atrial blood glucose sensor, an atrial contractility sensor, an atrial acoustic sensor and an atrial pressure sensor. As described above, in addition to storing IEGM data in response to a sensor-based trigger, the pacer/ICD may be programmed to also store data from the sensor that triggered the storage of the IEGM data. Still further, other arrhythmias that are not strictly regarded as atrial in origin (such as SVT, ST, AVRT, AVNRT) might nevertheless be classified or designated as "atrial" by the physician for the purposes of triggering storage of atrial IEGMs. Further, in some implementations, it may be appropriate to provide additional designations beyond "atrial-related" and "ventricular-related," such as supraventricular-related.

Meanwhile, at step 304, the pacer/ICD receives and stores a user selection of ventricular-based triggers to be used to trigger storage of IEGMs and other diagnostic data. The choice of ventricular-related triggers again depends upon the capabilities of the device. In a typical example, the pacer/ICD is at least capable of detecting VT, VF and consecutive PVCs and so corresponding triggers can be selected by the user. Other ventricular-related triggers may be specified based on the detection capabilities of the device. For example, if the pacer/ICD is capable of detecting, e.g., idiopathic RV tachycardia, idiopathic LV tachycardia, and/or ventricular bigeminy, trigeminy, quadrigeminy, etc., then corresponding ventricular-related triggers can be selected. In general, any ventricular-based event detectable by the pacer/ICD within the electrical cardiac signals of the heart can be employed as a ventricular-related trigger, whether the event constitutes a ventricular arrhythmia or otherwise. Moreover, if the device is equipped with one or more ventricular-based physiological sensors, then various non-cardiac signal-based ventricular triggers can be specified. Exemplary sensors that might be implanted on or in the ventricles include: a ventricular blood oxygen sensor, a ventricular pH sensor, a ventricular temperature sensor, a ventricular blood glucose sensor, a ventricular contractility sensor, a ventricular acoustic sensor, a ventricular pressure sensor, and a cardiac output sensor. As above, the pacer/ICD might be programmed to store data from the sensor that triggered the storage of the IEGM data. As with the atrial-related triggers discussed above, various arrhythmias that are not strictly regarded as ventricular in origin (such as SVT) might nevertheless be classified or designated as "ventricular" by the physician for the purposes of triggering storage of ventricular IEGMs. Indeed, some arrhythmias (such as those of supraventricular origin) might be classified as both atrial-based and ventricular-based by the physician so as to trigger the recording of both atrial IEGMs and ventricular IEGMs, based on the capabilities and programming of the pacer/ICD.

The various user selections of steps 300-304 may initially be provided by a physician or other clinician via an external programmer. Then, beginning at step 306, the pacer/ICD senses IEGM signals on each of the four sensing channels using the four electrode pairs selected at step 300 and analyzes the IEGM signals to detect any triggers. Assuming no triggers are detected, step 306 is simply repeated to sense and analyze additional IEGM signals. However, once an atrial or ventricular trigger is detected, processing continues in FIG. 6 where the pacer/ICD records diagnostic data appropriate either to atrial-related events or ventricular-related events.

More specifically, if an atrial-related trigger was detected, step 308 is next performed wherein the pacer/ICD stores the two atrial channel IEGMS along with only the primary ventricular channel IEGM. Thus, in response to atrial-related triggers, both of the atrial channels are recorded to record IEGMs; whereas only the primary ventricular channel is recorded. It should be understood that the pacer/ICD continues to sense IEGM data using all four pairs of electrodes. At step 310, the pacer/ICD the pacer/ICD determines whether the atrial diagnostics interval is complete and, if not, returns to step 308 for further sensing. The atrial-related diagnostics interval specifies how long the pacer/ICD will record IEGMs in response to an atrial-related trigger. Once the atrial diagnostics interval is complete, the pacer/ICD deactivates IEGM recording and returns to step 306 of FIG. 5 for further sensing using all four pairs of electrodes. Conversely, if a ventricular-related trigger was detected, step 312 is instead performed wherein the pacer/ICD stores the two ventricular channel IEGMS along with only the primary atrial channel IEGM. Hence, in response to ventricular-related triggers, both of the ventricular channels are used to record IEGMs; whereas only the primary atrial channel is used. It again should be understood that the pacer/ICD continues to sense IEGMs using all four pairs of electrodes. At step 314, the pacer/ICD determines whether the ventricular diagnostics interval is complete and, if not, returns to step 312 for further sensing. Once the ventricular diagnostics interval is complete, the pacer/ICD deactivates IEGM recording and returns to step 306 of FIG. 5 for further sensing using all four pairs of electrodes.

As with the generalized embodiment described above, while sensing and recording IEGMs during the atrial and ventricular diagnostics intervals, the pacer/ICD may also deliver therapy in response to the condition that triggered the diagnostics recording. Moreover, the pacer/ICD also continues to monitor the cardiac signals to detect additional triggers and, in particular, to detect the onset of potentially more serious arrhythmias or other conditions and deliver appropriate therapy. Still further, the pacer/ICD may be programmed to automatically switch from atrial channel IEGM recording (of steps 308-310) to ventricular channel IEGM recording (of steps 312-314) in response to detection of a ventricular-related trigger during atrial channel diagnostics. That is, if a ventricular trigger is detected during the operation of steps 308-310, the pacer/ICD automatically switches to steps 312-314. As noted above, overlap recording of IEGMs can instead be exploited.

Thus, FIGS. 5 and 6, illustrate an implementation where the pacer/ICD records two atrial and one ventricular channel of IEGM signals in response to atrial-related triggers and instead records two ventricular and one atrial channel of IEGM signals in response to ventricular-related triggers. In this manner, the physician is provided with a total of three IEGMs in response to each trigger event, with the particular IEGMs automatically selected based on the chambers in which the event occurred. The device saves memory resources by recording only three of the four sensed IEGM channels.

Other arrangements can be employed. For example, a device may be provided that is capable of sensing two IEGMs at once—one atrial and one ventricular—but is capable of recording only one IEGM. In such an implementation, the physician specifies a single atrial channel and a single ventricular channel for use in sensing IEGMs. Whenever an atrial-related trigger is detected, the atrial channel IEGM is recorded. In contrast, whenever a ventricular-related trigger is detected, the ventricular channel IEGM is recorded. In general, any arbitrary number of channels can be sensed and any arbitrary number of channels can be recorded, limited only by the capabilities of the device. Moreover, the triggers can be further classified based on the left and right chambers. That is, certain atrial triggers may be classified as being left atrial-triggers or right atrial-triggers; whereas certain ventricular triggers may be classified as being left ventricular-triggers or right ventricular-triggers. Examples include an idiopathic RV tachycardia-trigger and an idiopathic LV tachycardia-trigger. Particular IEGMs are then automatically selected for storage that emphasize the specific chamber depending upon the trigger, such as an LV-IEGM recorded in response to idiopathic LV tachycardia or a RV-IEGM recorded in response to idiopathic RV tachycardia. If physiologic sensors are provided that are specific to particular chambers, such as a left atrial pressure (LAP) sensor or a right atrial pressure (RAP) sensor, data from the sensors may also be selectively recorded based on the chamber-specific trigger. As can be appreciated, a wide range of options are available in accordance with the general principles of the invention.

Pre-Trigger Example of Trigger-Specific IEGM Recording Techniques

Figure 7:
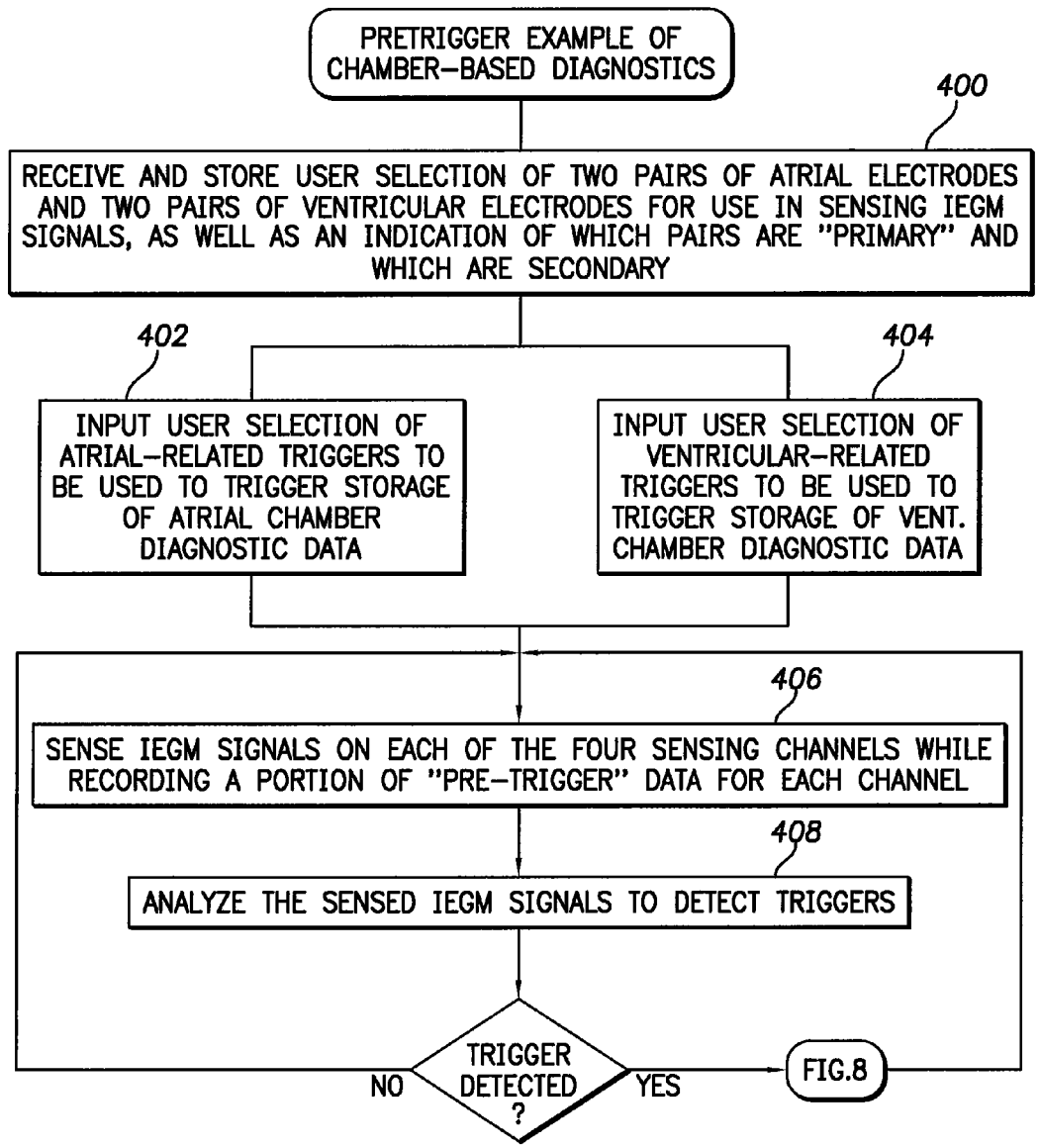
FIG. 7 is a flow chart providing a pre-trigger recording example of the trigger-specific IEGM recording techniques of FIG. 2.

FIG. 7 provides a four channel example of wherein pre-trigger IEGMs are also recorded. As with the previous example, the implantable medical system supports two default atrial sensing channels and two default ventricular sensing channels. Many of the steps of FIG. 7 are similar to those of the preceding figures and only pertinent differences will be described in detail. At step 400, the pacer/ICD receives and stores a user selection of two pairs of atrial electrodes (shorted or otherwise) and two pairs of ventricular electrodes (shorted or otherwise) for use in sensing IEGM signals, as well as an indication of which pairs are primary and which are secondary. At step 402, the pacer/ICD receives and stores a user selection of atrial-based triggers to be used to trigger storage of IEGMs and other diagnostic data during an atrial diagnostics interval. Again, the choice of atrial-related triggers depends upon the capabilities of the device. Meanwhile, at step 404, the pacer/ICD receives and stores a user selection of ventricular-based triggers to be used to trigger storage of IEGMs and other diagnostic data. The choice of ventricular-related triggers likewise depends upon the capabilities of the device.

Then, beginning at step 406, the pacer/ICD senses IEGM signals on each of the four sensing channels using the four electrode pairs selected at step 400 while recording a portion of "pre-trigger" IEGM data for each of the four channels within pre-trigger FIFO memory. For example, the pacer/ICD may be programmed to record one minute of IEGM data on each of the four channels in the FIFO memory. (In other implementations, pretrigger data is recorded for all possible sensing channels, including all possible combinations of electrodes, depending upon the capabilities of the pacer/ICD and its memory resources.) At step 408, the pacer/ICD analyzes the IEGM signals sensed at step 406 to detect atrial or ventricular triggers, if any. Assuming no triggers are detected, steps 406 and 408 are simply repeated to sense and analyze additional IEGM signals and to update the pre-trigger memory with newly recorded IEGM data. However, once an atrial or ventricular trigger is detected, processing continues in FIG. 8.

In this regard, if an atrial-related trigger was detected, step 410 is next performed wherein the pacer/ICD transfers the two atrial channels of pretrigger IEGM data and the primary ventricular channel of pre-trigger IEGM data from the pre-trigger memory to separate long-term memory. Then, at step 412, the pacer/ICD senses and stores additional IEGM data from the two atrial channels and from the primary ventricular channel IEGM. Thus, in response to atrial-related triggers, pre-trigger and post-trigger IEGM data is saved for both atrial channels and for the primary ventricular channel. It should be understood that the pacer/ICD continues to sense using all four pairs of electrodes. (Preferably, newly sensed IEGM data from all four channels is stored in the pre-trigger memory even during the diagnostics interval to keep the pretrigger memory up to date.) At step 414, the pacer/ICD determines whether the atrial diagnostics interval is complete and, if not, returns to step 410 for further sensing. Once the atrial diagnostics interval is complete, the pacer/ICD deactivates IEGM recording and returns to step of 406 of FIG. 7 for further sensing using all four pairs of electrodes and for further recording of pre-trigger data.

Conversely, if a ventricular-related trigger was detected, step 416 is next performed wherein the pacer/ICD transfers the two ventricular channels of pretrigger IEGM data and the primary atrial channel of pre-trigger IEGM data from the pretrigger memory to separate long-term memory. Then, at step 418, the pacer/ICD senses and stores additional IEGM data from the two ventricular channels and from the primary atrial channel IEGM. Thus, in response to ventricular-related triggers, pre-trigger and post-trigger IEGM data is saved for both ventricular channels and for the primary atrial channel. It again should be understood that the pacer/ICD continues to sense using all four pairs of electrodes during the diagnostics intervals and that, preferably, newly sensed IEGM data from all four channels is stored in pre-trigger memory to keep the pretrigger memory up to date. At step 420, the pacer/ICD determines whether the ventricular diagnostics interval is complete and, if not, returns to step 416 for further sensing. Once the ventricular diagnostics interval is complete, the pacer/ICD deactivates IEGM recording and returns to step of 406 of FIG. 7 for further sensing using all four pairs of electrodes and for further recording of pre-trigger data.

As with the embodiments described above, while sensing and recording IEGMs during the atrial and ventricular diagnostics intervals, the pacer/ICD may also deliver therapy in response to the condition that triggered the diagnostics recording. Moreover, the pacer/ICD also continues to monitor the cardiac signals to detect additional triggers and, in particular, to detect the onset of potentially more serious arrhythmias or other conditions and deliver appropriate therapy. Still further, the pacer/ICD may be programmed to switch from atrial channel IEGM recording (of steps 410-414) to ventricular channel IEGM recording (of steps 416-420) in response to detection of a ventricular-related trigger during atrial channel diagnostics. By keeping the pre-trigger memory up to date, even during the diagnostic interval, the pacer/ICD can ensure that the appropriate pre-trigger IEGM data can be saved should a switch from atrial channel IEGM recording to ventricular channel IEGM recording be required.

Figure 8:
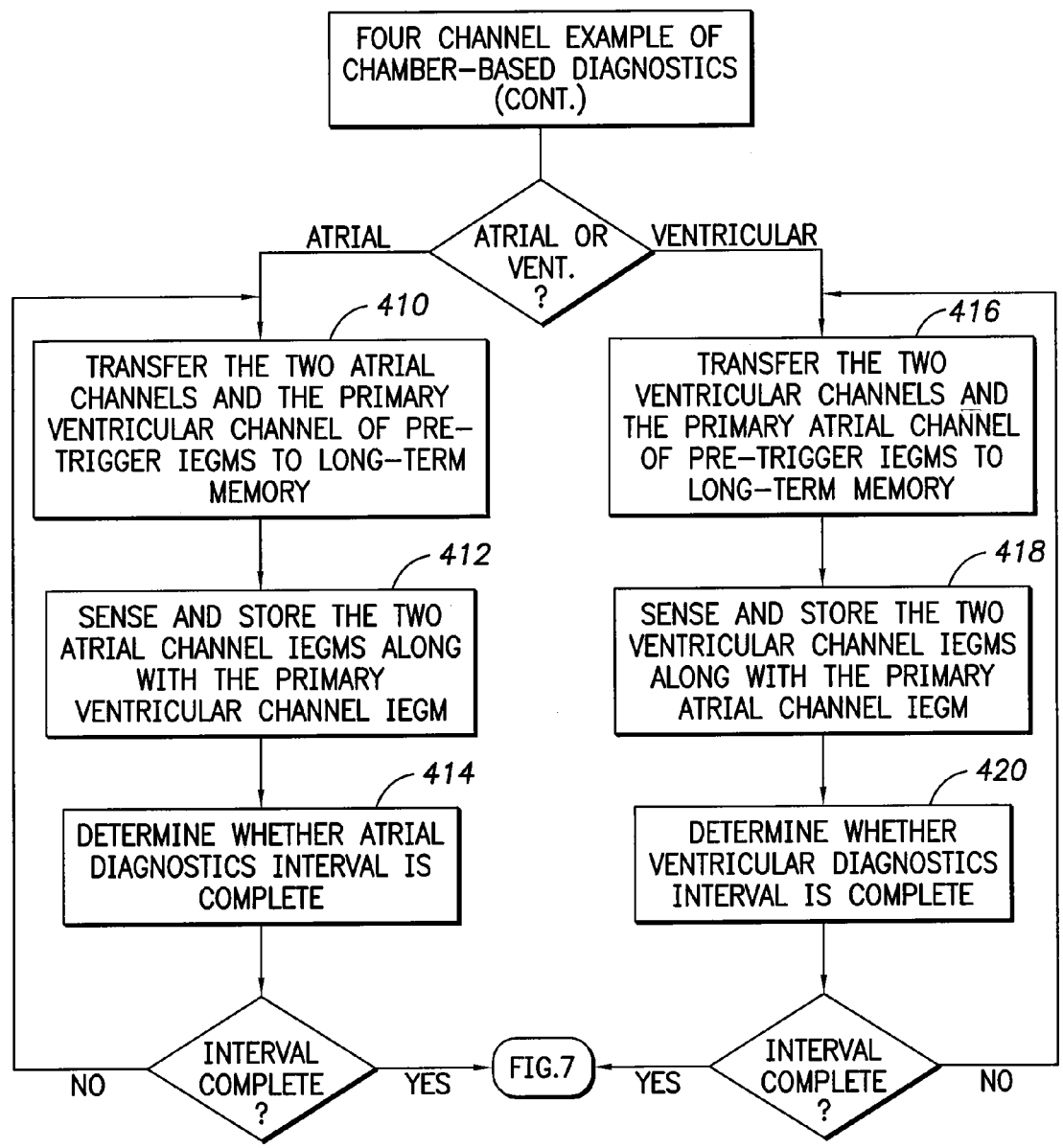
FIG. 8 is a flow chart illustrating post-trigger recording steps for use with the pre-trigger example of FIG. 7.

Thus, FIGS. 7 and 8, illustrate an implementation where the pacer/ICD saves two atrial channels and one ventricular channel of pre-trigger IEGM signals in response to atrial-related triggers and instead saves two ventricular channels and one atrial channel of pre-trigger IEGM signals in response to atrial-related triggers. In this manner, the physician is provided with a total of three channels of pre-trigger and post-trigger IEGMs in response to each trigger event, with the particular IEGMs automatically selected based on the chambers in which the event occurred. The device saves memory resources by recording only three of the four sensed IEGM channels. Other arrangements can be employed, as explained above, wherein more or fewer channels are employed or wherein data from physiological sensors is additionally saved.

Although primarily described with respect to examples having a pacer/ICD, other implantable medical devices may be equipped to exploit the techniques described herein. For the sake of completeness, an exemplary pacer/ICD will now be described, which includes components for performing the functions and steps already described. Also, an exemplary external programmer will be described, which includes components for performing the calibration steps already described.

Exemplary Pacemaker/ICD

FIG. 9 provides a simplified block diagram of the pacer/ICD, which is a multi-chamber stimulation device capable of treating both fast and slow arrhythmias with stimulation therapy, including cardioversion, defibrillation, and pacing stimulation (as well as capable of performing trigger-specific diagnostics recording.) To provide atrial chamber pacing stimulation and sensing, pacer/ICD 10 is shown in electrical communication with a heart 512 by way of a left atrial lead 520 having an atrial tip electrode 522 and an atrial ring electrode 523 implanted in the atrial appendage. Pacer/ICD 10 is also in electrical communication with the heart by way of a right ventricular lead 530 having, in this embodiment, a ventricular tip electrode 532, a right ventricular ring electrode 534, a right ventricular (RV) coil electrode 536, and a superior vena cava (SVC) coil electrode 538. Typically, the right ventricular lead 530 is transvenously inserted into the heart so as to place the RV coil electrode 536 in the right ventricular apex, and the SVC coil electrode 538 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 524 designed for placement in the "coronary sinus region" via the coronary sinus is for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 524 is designed to receive atrial and ventricular cardiac signals and to deliver left ventricular pacing therapy using at least a left ventricular ring electrode 525, a left ventricular tip electrode 526, left atrial pacing therapy using at least a left atrial ring electrode 527, and shocking therapy using at least a left atrial coil electrode 528. With this configuration, biventricular pacing can be performed. Although only three leads are shown in FIG. 9, it should also be understood that additional stimulation leads (with one or more pacing, sensing and/or shocking electrodes) may be used in order to efficiently and effectively provide pacing stimulation to the left side of the heart or atrial cardioversion and/or defibrillation.

Figure 10:
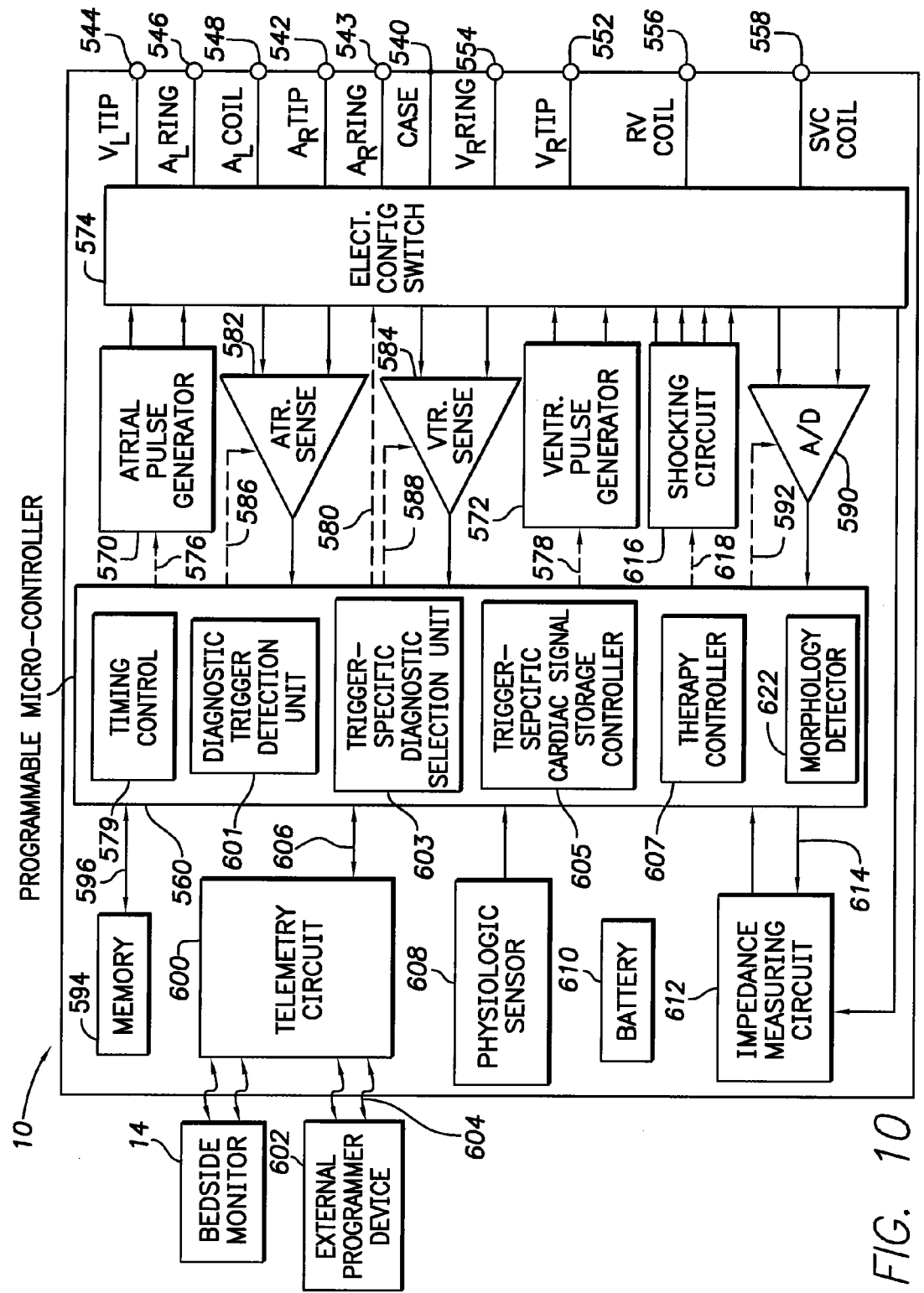
FIG. 10 is a functional block diagram of the pacer/ICD of FIG. 9, illustrating basic circuit elements that provide cardioversion, defibrillation and/or pacing stimulation in four chambers of the heart, and particularly illustrating components for controlling trigger-specific recording of IEGMs and other diagnostic data.

A simplified block diagram of internal components of pacer/ICD 10 is shown in FIG. 10. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy. The housing 540 for pacer/ICD 10, shown schematically in FIG. 10, is often referred to as the "can", "case" or "case electrode" and may be programmably selected to act as the return electrode for all "unipolar" modes. The housing 540 may further be used as a return electrode alone or in combination with one or more of the coil electrodes, 528, 536 and 538, for shocking purposes. The housing 540 further includes a connector (not shown) having a plurality of terminals, 542, 543, 544, 546, 548, 552, 554, 556 and 558 (shown schematically and, for convenience, the names of the electrodes to which they are connected are shown next to the terminals). As such, to achieve right atrial sensing and pacing, the connector includes at least a right atrial tip terminal ($A_R$ TIP) 542 adapted for connection to the atrial tip electrode 522 and a right atrial ring ($A_R$ RING) electrode 543 adapted for connection to right atrial ring electrode 543. To support sensing, pacing and shocking in the left atrial and ventricular chambers of the heart, the connector includes at least a left ventricular tip terminal ($V_L$ TIP) 544, a left atrial ring terminal ($A_L$ RING) 546, and a left atrial shocking terminal ($A_L$ COIL) 548, which are adapted for connection to the left ventricular ring electrode 526, the left atrial tip electrode 527, and the left atrial coil electrode 528, respectively. To support sensing, pacing and shocking in the right atrial and ventricular chambers of the heart, the connector further includes a right ventricular tip terminal ($V_R$ TIP) 552, a right ventricular ring terminal ($V_R$ RING) 554, a right ventricular shocking terminal ($R_V$ COIL) 556, and an SVC shocking terminal (SVC COIL) 558, which are adapted for connection to the right ventricular tip electrode 532, right ventricular ring electrode 534, the RV coil electrode 536, and the SVC coil electrode 538, respectively.

At the core of pacer/ICD 10 is a programmable microcontroller 560, which controls the various modes of stimulation therapy. As is well known in the art, the microcontroller 560 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 560 includes the ability to process or monitor input signals (data) as controlled by a program code stored in a designated block of memory. The details of the design and operation of the microcontroller 560 are not critical to the invention. Rather, any suitable microcontroller 560 may be used that carries out the functions described herein. The use of microprocessor-based control circuits for performing timing and data analysis functions are well known in the art.

As shown in FIG. 10, an atrial pulse generator 570 and a ventricular/impedance pulse generator 572 generate pacing stimulation pulses for delivery by the right atrial lead 520, the right ventricular lead 530, and/or the coronary sinus lead 524 via an electrode configuration switch 574. It is understood that in order to provide stimulation therapy in each of the four chambers of the heart, the atrial and ventricular pulse generators, 570 and 572, may include dedicated, independent pulse generators, multiplexed pulse generators or shared pulse generators. The pulse generators, 570 and 572, are controlled by the microcontroller 560 via appropriate control signals, 576 and 578, respectively, to trigger or inhibit the stimulation pulses.

The microcontroller 560 further includes timing control circuitry 579 used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 574 includes a plurality of switches for connecting the desired electrodes to the appropriate I/O circuits, thereby providing complete electrode programmability. Accordingly, the switch 574, in response to a control signal 580 from the microcontroller 560, determines the polarity of the stimulation pulses (e.g., unipolar, bipolar, combipolar, etc.) by selectively closing the appropriate combination of switches (not shown) as is known in the art.

Atrial sensing circuits 582 and ventricular sensing circuits 584 may also be selectively coupled to the right atrial lead 520, coronary sinus lead 524, and the right ventricular lead 530, through the switch 574 for detecting the presence of cardiac activity in each of the four chambers of the heart. Accordingly, the atrial (ATR. SENSE) and ventricular (VTR. SENSE) sensing circuits, 582 and 584, may include dedicated sense amplifiers, multiplexed amplifiers or shared amplifiers. The sensing circuits are preferably equipped to provide at least two atrial sensing channels and two ventricular sensing channels. The switch 574 determines the "sensing polarity" of the cardiac signal by selectively closing the appropriate switches, as is also known in the art. In this way, the clinician may program the sensing polarity independent of the stimulation polarity. Each sensing circuit, 582 and 584, preferably employs one or more low power, precision amplifiers with programmable gain and/or automatic gain control and/or automatic sensitivity control, bandpass filtering, and a threshold detection circuit, as known in the art, to selectively sense the cardiac signal of interest. The outputs of the atrial and ventricular sensing circuits, 582 and 584, are connected to the microcontroller 560 which, in turn, are able to trigger or inhibit the atrial and ventricular pulse generators, 570 and 572, respectively, in a demand fashion in response to the absence or presence of cardiac activity in the appropriate chambers of the heart.

For arrhythmia detection, pacer/ICD 10 utilizes the atrial and ventricular sensing circuits, 582 and 584, to sense cardiac signals to determine whether a rhythm is physiologic or pathologic. As used in this section "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 560 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 590. The data acquisition system 590 is configured to acquire intracardiac electrogram signals, convert the raw analog data into a digital signal, and store the digital signals for later processing and/or telemetric transmission to an external device or instrument 602. The data acquisition system 590 is coupled to the right atrial lead 520, the coronary sinus lead 524, and the right ventricular lead 530 through the switch 574 to sample cardiac signals across any pair of desired electrodes. The microcontroller 560 is further coupled to a memory 594 by a suitable data/address bus 596, wherein the programmable operating parameters used by the microcontroller 560 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart. Other pacing parameters include base rate, rest rate and circadian base rate.

Advantageously, the operating parameters of the implantable pacer/ICD 10 may be non-invasively programmed into the memory 594 through a telemetry circuit 600 in telemetric communication with the external device 602, such as a programmer, transtelephonic transceiver or a diagnostic system analyzer. The telemetry circuit 600 is activated by the microcontroller by a control signal 606. The telemetry circuit 600 advantageously allows intracardiac electrograms and status information relating to the operation of pacer/ICD 10 (as contained in the microcontroller 560 or memory 594) to be sent to the external device 602 through an established communication link 604. Pacer/ICD 10 further includes an accelerometer or other physiologic sensor 608, commonly referred to as a "rate-responsive" sensor because it is typically used to adjust pacing stimulation rate according to the exercise state of the patient. However, the physiological sensor 608 may, depending upon its capabilities, further be used to detect changes in cardiac output, changes in the physiological condition of the heart, or diurnal changes in activity (e.g., detecting sleep and wake states) and to detect arousal from sleep. Accordingly, the microcontroller 560 responds by adjusting the various pacing parameters (such as rate, AV Delay, V-V Delay, etc.) at which the atrial and ventricular pulse generators, 570 and 572, generate stimulation pulses. While shown as being included within pacer/ICD 10, it is to be understood that the sensor 608 may also be external to pacer/ICD 10, yet still be implanted within or carried by the patient. A common type of rate responsive sensor is an activity sensor incorporating an accelerometer or a piezoelectric crystal, which is mounted within the housing 540 of pacer/ICD 10. Other types of physiologic sensors are also known, for example, sensors that sense the oxygen content of blood, respiration rate and/or minute ventilation, blood pH, ventricular gradient, cardiac output, blood glucose, blood temperature, heart wall contractility, as well as acoustic sensors and pressure sensors. As noted above, the sensor may be chamber-specific, depending upon the location of the actual sensing components.

The pacer/ICD additionally includes a battery 610, which provides operating power to all of the circuits shown in FIG. 10. The battery 610 may vary depending on the capabilities of pacer/ICD 10. If the system only provides low voltage therapy, a lithium iodine or lithium copper fluoride cell may be utilized. For pacer/ICD 10, which employs shocking therapy, the battery 610 should be capable of operating at low current drains for long periods, and then be capable of providing high-current pulses (for capacitor charging) when the patient requires a shock pulse. The battery 610 should also have a predictable discharge characteristic so that elective replacement time can be detected. Accordingly, pacer/ICD 10 is preferably capable of high voltage therapy and batteries or other power sources appropriate for that purpose are employed.

As further shown in FIG. 10, pacer/ICD 10 is shown as having an impedance measuring circuit 612, which is enabled by the microcontroller 560 via a control signal 614. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 612 is advantageously coupled to the switch 574 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 560 further controls a shocking circuit 616 by way of a control signal 618. The shocking circuit 616 generates shocking pulses of low (up to 0.5 joules), moderate (0.5-10 joules) or high energy (11 to about 40 joules), as controlled by the microcontroller 560. Such shocking pulses are applied to the heart of the patient through at least two shocking electrodes, and as shown in this embodiment, selected from the left atrial coil electrode 528, the RV coil electrode 536, and/or the SVC coil electrode 538. The housing 540 may act as an active electrode in combination with the RV electrode 536, or as part of a split electrical vector using the SVC coil electrode 538 or the left atrial coil electrode 528 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 to about 40 joules), delivered asynchronously (since R-waves may be too disorganized), and pertaining exclusively to the treatment of fibrillation. Accordingly, the microcontroller 560 is capable of controlling the synchronous or asynchronous delivery of the shocking pulses.

Microcontroller 560 also includes a diagnostic trigger detection unit 601 operative to detect the occurrence of a particular trigger within signals sensed by sensing circuits 582 and 584. A trigger-specific diagnostic selection unit 603 is operative to identify cardiac signals selected by a user for storage based on the trigger detected by the detection unit. In one example, user selections of particular cardiac signals to be stored for each of a plurality of diagnostic triggers are maintained in memory 594. (That is, a portion of the memory provides a user selection storage unit operative to store an indication of particular cardiac signals to be stored in response to particular diagnostic triggers.) A trigger-specific cardiac signal storage controller 605 is operative to control the storage of the particular cardiac signal data identified by the diagnostic selection unit 603 in response to a detected trigger. The cardiac signal data is actually stored in memory 594. These components preferably operate in accordance with the techniques summarized above with reference to FIGS. 1-8. Any therapy to be provided in response to detected arrhythmias (or other triggers) is controlled by a therapy controller 607. Depending upon the implementation, the various components illustrated within the microcontroller may be implemented as separate hardware or software modules. However, the modules may be combined so as to permit single modules to perform multiple functions.

Exemplary External Programmer

Figure 11:
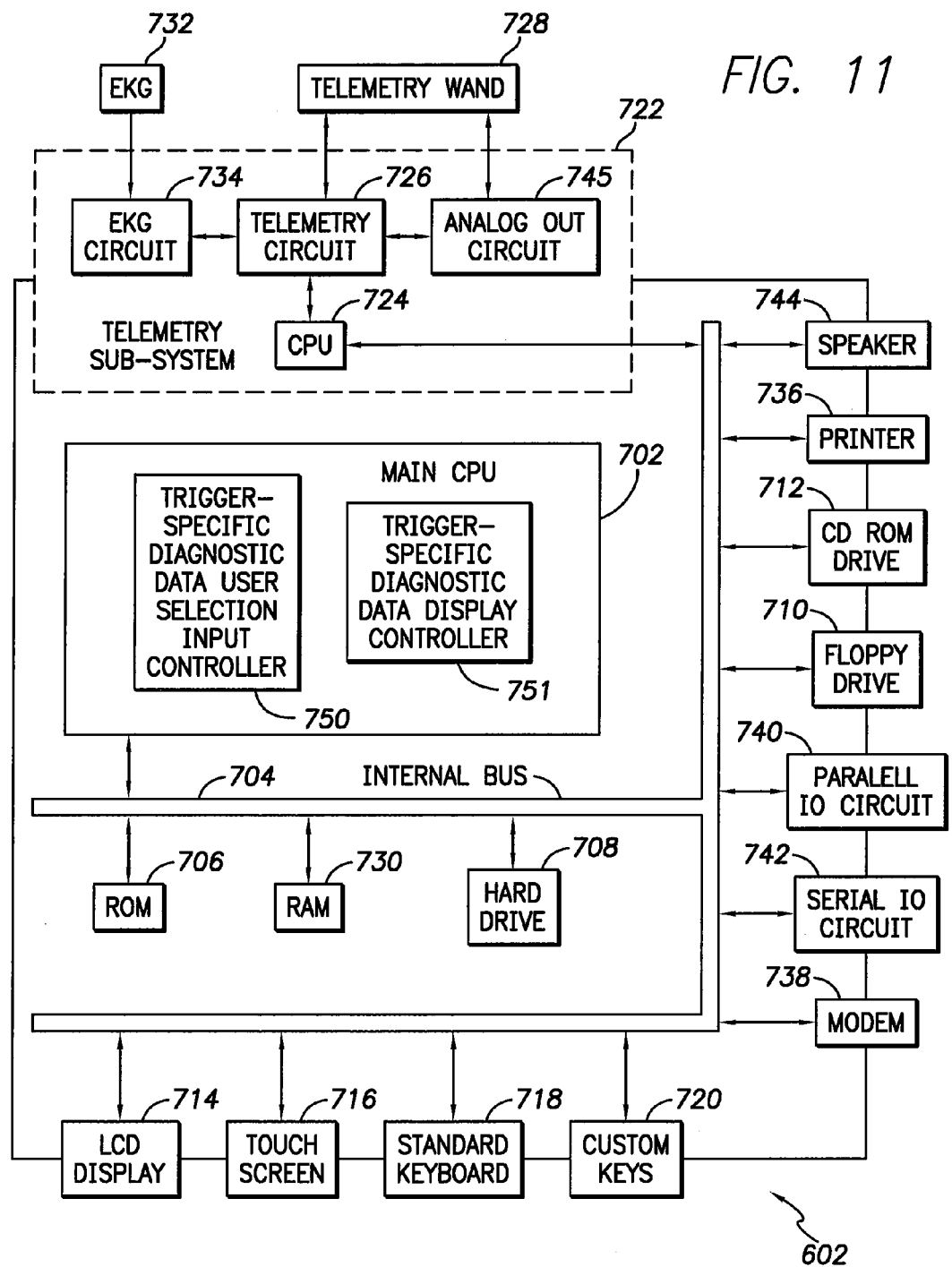
FIG. 11 is a functional block diagram illustrating components of a device programmer for use in programming the pacer/ICD of FIG. 10, and in particular illustrating components for inputting an indication of particular IEGMs to be stored in response to particular diagnostic triggers for use in programming the pacer/ICD and also components for displaying resulting IEGMs received from the pacer/ICD.

FIG. 11 illustrates pertinent components of an external programmer 602 for use in programming the pacer/ICD of FIG. 10 and, in particular, for controlling the above-described trigger-specific diagnostic techniques. For the sake of completeness, other device programming functions are also described herein. Generally, the programmer permits a physician or other user to program the operation of the implanted device and to retrieve and display information received from the implanted device such as IEGM data and device diagnostic data. Additionally, the external programmer can be optionally equipped to receive and display electrocardiogram (EKG) data from separate external EKG leads that may be attached to the patient. Depending upon the specific programming of the external programmer, programmer 602 may also be capable of processing and analyzing data received from the implanted device and from the EKG leads to, for example, render preliminary diagnosis as to medical conditions of the patient or to the operations of the implanted device.

Now, considering the components of programmer 602, operations of the programmer are controlled by a CPU 702, which may be a generally programmable microprocessor or microcontroller or may be a dedicated processing device such as an application specific integrated circuit (ASIC) or the like. Software instructions to be performed by the CPU are accessed via an internal bus 704 from a read only memory (ROM) 706 and random access memory 730. Additional software may be accessed from a hard drive 708, floppy drive 710, and CD ROM drive 712, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 714 or other suitable computer display device. To this end, the CPU may, for example, display a menu of specific programmable parameters of the implanted device to be programmed or may display a menu of types of diagnostic data to be retrieved and displayed. In response thereto, the physician enters various commands via either a touch screen 716 overlaid on the LCD display or through a standard keyboard 718 supplemented by additional custom keys 720, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

Once all pacing leads are mounted and the pacing device is implanted, the various parameters are programmed. Typically, the physician initially controls the programmer 602 to retrieve data stored within any implanted devices and to also retrieve EKG data from EKG leads, if any, coupled to the patient. To this end, CPU 702 transmits appropriate signals to a telemetry subsystem 722, which provides components for directly interfacing with the implanted devices, and the EKG leads. Telemetry subsystem 722 includes its own separate CPU 724 for coordinating the operations of the telemetry subsystem. Main CPU 702 of programmer communicates with telemetry subsystem CPU 724 via internal bus 704. Telemetry subsystem additionally includes a telemetry circuit 726 connected to telemetry wand 728, which, in turn, receives and transmits signals electromagnetically from a telemetry unit of the implanted device. The telemetry wand is placed over the chest of the patient near the implanted device to permit reliable transmission of data between the telemetry wand and the implanted device. Herein, the telemetry subsystem is shown as also including an EKG circuit 734 for receiving surface EKG signals from a surface EKG system 732. In other implementations, the EKG circuit is not regarded as a portion of the telemetry subsystem but is regarded as a separate component.

Typically, at the beginning of the programming session, the external programming device controls the implanted devices via appropriate signals generated by the telemetry wand to output all previously recorded patient and device diagnostic information. Patient diagnostic information includes, for example, the aforementioned trigger-specific IEGM data as well as statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the implanted devices is stored by external programmer 602 either within a random access memory (RAM) 730, hard drive 708 or within a floppy diskette placed within floppy drive 710. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted devices is transferred to programmer 602, the implanted devices may be further controlled to transmit additional data in real time as it is detected by the implanted devices, such as additional IEGM data, lead impedance data, and the like. Additionally, or in the alternative, telemetry subsystem 722 receives EKG signals from EKG leads 732 via an EKG processing circuit 734. As with data retrieved from the implanted device itself, signals received from the EKG leads are stored within one or more of the storage devices of the external programmer. Typically, EKG leads output analog electrical signals representative of the EKG. Accordingly, EKG circuit 734 includes analog to digital conversion circuitry for converting the signals to digital data appropriate for further processing within the programmer. Depending upon the implementation, the EKG circuit may be configured to convert the analog signals into event record data for ease of processing along with the event record data retrieved from the implanted device. Typically, signals received from the EKG leads are received and processed in real time.

Thus, the programmer receives data both from the implanted devices and from optional external EKG leads. Data retrieved from the implanted devices includes parameters representative of the current programming state of the implanted devices. Under the control of the physician, the external programmer displays the current programmable parameters and permits the physician to reprogram the parameters. To this end, the physician enters appropriate commands via any of the aforementioned input devices and, under control of CPU 702, the programming commands are converted to specific programmable parameters for transmission to the implanted devices via telemetry wand 728 to thereby reprogram the implanted devices. Prior to reprogramming specific parameters, the physician may control the external programmer to display any or all of the data retrieved from the implanted devices or from the EKG leads, including displays of EKGs, IEGMs, and statistical patient information. Any or all of the information displayed by programmer may also be printed using a printer 736.

Additionally, CPU 702 also preferably includes a trigger-specific diagnostic data user selection input controller 750 operative to input an indication of particular cardiac signals to be recorded by the implantable medical device being programmed in response to particular diagnostic triggers detected within the patient. The user selections generally specify different cardiac signals to be recorded in response to different diagnostic triggers. The telemetry sub-system 722 then transmits the user selections to the implantable medical device and, during a follow-up session, receives a plurality of trigger-specific cardiac signals that had been recorded by the implantable medical device in response to different triggers detected within the patient. CPU 702 also preferably includes a trigger-specific diagnostic data display controller 751 operative to control the display of the trigger-specific cardiac signals received from the implantable device along with an indication of the corresponding triggers.

Programmer/monitor 602 also includes a modem 738 to permit direct transmission of data to other programmers via the public switched telephone network (PSTN) or other interconnection line, such as a T1 line or fiber optic cable. Depending upon the implementation, the modem may be connected directly to internal bus 704 may be connected to the internal bus via either a parallel port 740 or a serial port 742. Other peripheral devices may be connected to the external programmer via parallel port 740 or a serial port 742 as well. Although one of each is shown, a plurality of input output (10) ports might be provided. A speaker 744 is included for providing audible tones to the user, such as a warning beep in the event improper input is provided by the physician. Telemetry subsystem 722 additionally includes an analog output circuit 745 for controlling the transmission of analog output signals, such as IEGM signals output to an EKG machine or chart recorder.

With the programmer configured as shown, a physician or other user operating the external programmer is capable of retrieving, processing and displaying a wide range of information received from the implanted devices, including trigger-specific IEGMs and to reprogram the implanted device if needed. The descriptions provided herein with respect to FIG. 11 are intended merely to provide an overview of the operation of programmer and are not intended to describe in detail every feature of the hardware and software of the programmer and is not intended to provide an exhaustive list of the functions performed by the programmer.

Figure 12:
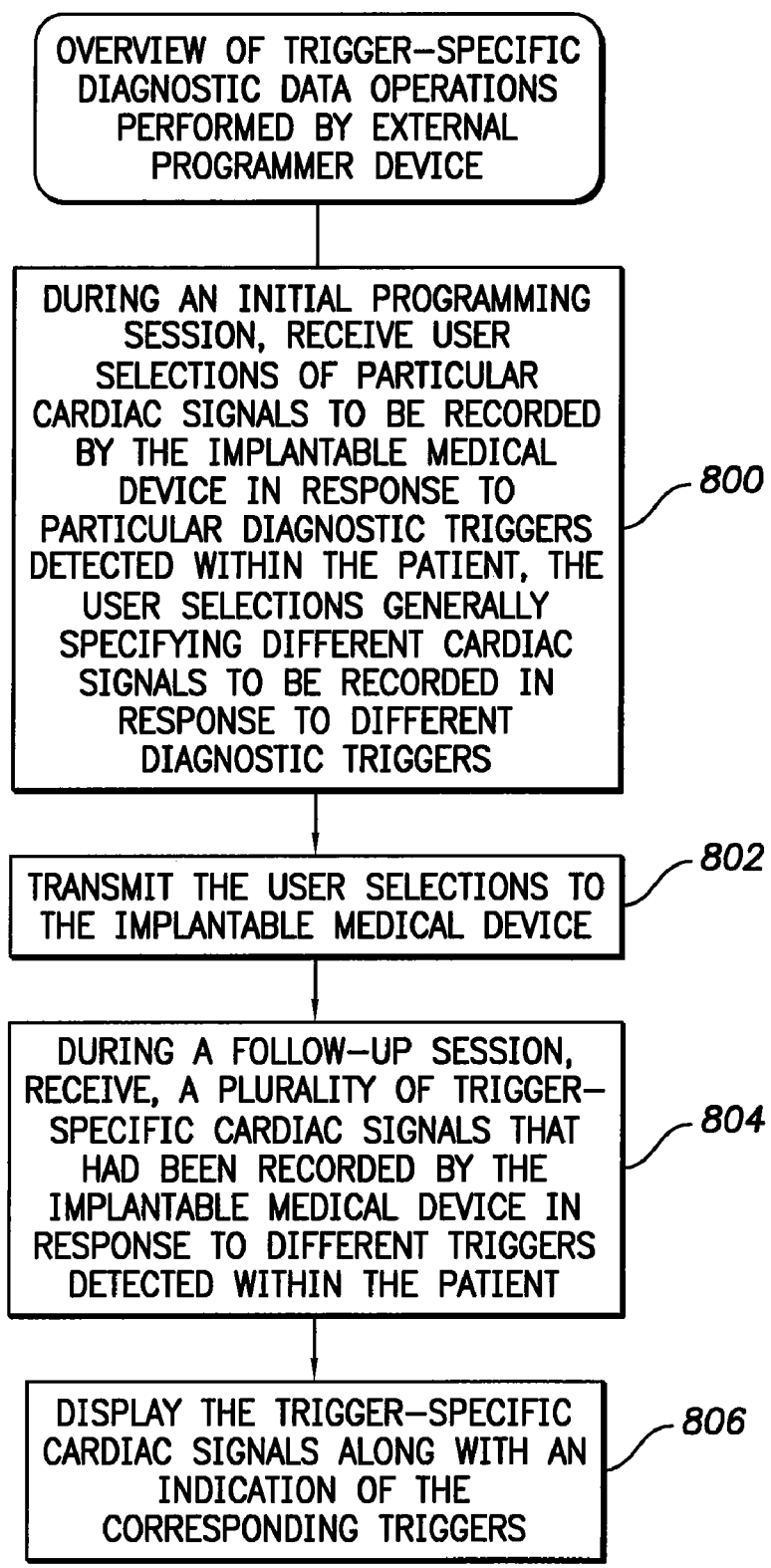
FIG. 12 is a flow diagram broadly summarizing the techniques performed by the external system of FIG. 11.

FIG. 12 provides a broad summary of the trigger-specific diagnostic recording control techniques performed by the programmer. Briefly, at step 800, during an initial programming session, the external programmer receives user selections of particular cardiac signals to be recorded by an implantable medical device implanted within a patient in response to particular diagnostic triggers detected within the patient. The user selections generally specify different cardiac signals to be recorded in response to different diagnostic triggers. At step 802, the programmer transmits the user selections to the implantable medical device. At step 804, during a follow-up session with the same patient, the external programmer receives a plurality of trigger-specific cardiac signals that had been recorded by the implantable medical device in response to different triggers detected within the patient. At step 806, the programmer then displays the trigger-specific cardiac signals along with an indication of the corresponding triggers.

While the invention has been described with reference to particular embodiments, modifications can be made thereto without departing from the scope of the invention. In particular, although described primarily with reference to an example wherein the implanted device is a pacer/ICD, principles of the invention are applicable to other implanted cardiac stimulation devices as well such as pacemakers without defibrillation capability or dedicated AF devices configured to detect AF and delivery therapy. (Some such devices only accommodate a single sensing channel and hence the techniques of the invention may not be appropriate. However, any device accommodating two or more sensing channels might benefit from the techniques of the invention.) Still other devices that might benefit from the invention include implantable medical devices for sensing signals of interest within other organs, such as the brain or kidneys, as well as non-implantable devices such as Holter monitors and the like. The various functional components of the exemplary systems may be implemented using any appropriate technology including, for example, microprocessors running software programs or application specific integrated circuits (ASICs) executing hard-wired logic operations. The exemplary embodiments of the invention described herein are merely illustrative of the invention and should not be construed as limiting the scope of the invention.

What is claimed is:

1. A method performed by an implantable medical device for controlling the recording of signals within a patient, wherein the device is capable of recording different types of signals in response to different diagnostic triggers, the method comprising:
   storing an indication of particular signals to be stored in response to particular diagnostic triggers;
   sensing signals within the patient;
   detecting the occurrence of a trigger within the patient;
   identifying, based on the particular detected trigger, the particular signals to be stored in response to the trigger;
   storing the particular signals identified for storage;
   wherein the signals are cardiac signals; and
   wherein the indication of particular cardiac signals to be stored in response to particular triggers specifies, for each trigger, at least one combination of electrodes for sensing the cardiac signals to be stored.

2. The method of claim 1 further including the initial step of receiving the indication of particular cardiac signals to be stored in response to particular diagnostic triggers from an external system.

3. The method of claim 2 wherein the indication of particular cardiac signals to be stored in response to particular diagnostic triggers is a user-specified indication.

4. The method of claim 2 further including the subsequent step of transmitting the stored cardiac signals to the external system for display.

5. The method of claim 1 wherein the cardiac signals to be stored comprise intracardiac electrograms (IEGMs).

6. The method of claim 1 wherein the electrodes include a plurality of: a right atrial tip electrode ($A_R$ TIP), a right atrial ring electrode ($A_R$ RING), a left ventricular tip electrode ($V_L$ TIP), a left atrial ring electrode ($A_L$ RING), a left atrial coil ($A_L$ COIL), a right ventricular tip electrode ($V_R$ TIP), a right ventricular ring electrode ($V_R$ RING), a right ventricular coil ($R_V$ COIL), a left ventricular tip electrode ($V_L$ TIP), a left ventricular ring electrode ($V_L$ RING), left ventricular coil ($V_L$ COIL) and a device housing electrode and shorted combinations thereof and wherein the indication of particular cardiac signals to be stored specifies the particular combinations of electrodes to be used to sense the cardiac signals to be stored in response to the particular diagnostic triggers.

7. The method of claim 1 wherein detecting the occurrence of a particular trigger within the patient includes detecting the trigger based on an analysis of the sensed cardiac signals.

8. The method of claim 7 wherein the triggers include one or more of: an automatic mode selection (AMS) trigger; a pacemaker mediated tachycardia (PMT) trigger; an atrial tachycardia (AT) trigger, an atrial fibrillation (AF) trigger, a ventricular tachycardia (VT) trigger, a ventricular fibrillation (VF) trigger and a consecutive preventricular contraction (PVC) trigger; an AF Shock trigger; a VF Shock trigger; a Return to Sinus trigger; a Commanded Shock trigger; a Magnet trigger; an Atrial Entry Into Noise trigger; a Ventricular Entry Into Noise trigger; an Atrial Exit From Noise trigger; a Ventricular Exit From Noise trigger; an Arrhythmia Induction trigger; a Loss Of Capture (LOC) trigger; an Automatic Activation of Morphological Template trigger; and a Sense Amplitude Test trigger.

9. The method of claim 1 wherein the implantable medical device is used in connection with at least one physiological sensor and wherein detecting the occurrence of a particular trigger includes detecting the trigger based on an analysis of signals provided by the physiological sensor.

10. The method of claim 9 wherein the sensor includes one or more of: a blood oxygen sensor, a pH sensor, a temperature sensor, a blood glucose sensor, an accelerometer, a cardiac output sensor, a contractility sensor, an acoustic sensor and a pressure sensor.

11. The method of claim 1 wherein the device is capable of storing pre-trigger cardiac signals and wherein the step of storing particular cardiac signals in response to a trigger is performed to selectively retain only those portions of the stored pre-trigger cardiac signals corresponding to the indication of particular cardiac signals to be stored in response to particular diagnostic triggers.

12. A method performed by an implantable medical device for controlling the recording of signals within a patient, wherein the device is capable of recording different types of signals in response to different diagnostic triggers, the method comprising:
   storing an indication of particular signals to be stored in response to particular diagnostic triggers;
   sensing signals within the patient;
   detecting the occurrence of a trigger within the patient;
   identifying, based on the particular detected trigger, the particular signals to be stored in response to the trigger;
   storing the particular signals identified for storage;
   wherein the signals are cardiac signals; and
   wherein the diagnostic triggers are classified as either atrial-related triggers or ventricular-related triggers and wherein the indication of particular cardiac signals to be stored in response to particular diagnostic triggers identifies the particular cardiac signals to be stored for atrial-related triggers and for ventricular-related triggers.

13. A system for controlling the recording of signals within an implantable medical device capable of recording different types of signals in response to various diagnostic triggers, the system comprising:
   a storage unit operative to store an indication of particular signals to be stored in response to particular diagnostic triggers;
   a sensing system operative to sense signals;

a diagnostic trigger detection unit operative to detect the occurrence of a particular trigger within the patient;

a trigger-specific diagnostic selection unit operative to identify the particular signals to be stored based on the trigger detected by the diagnostic trigger detection unit and by the indication of particular signals stored by the storage unit;

a trigger-specific signal storage controller operative to control the storage of the particular signals identified by the diagnostic selection unit; wherein the signals are cardiac signals; and the trigger-specific diagnostic selection unit specifies, for each trigger, at least one combination of electrodes for sensing the cardiac signals to be stored.

14. The system of claim 13 wherein the implantable medical device is capable of recording different types of cardiac signals in response to various diagnostic triggers, and wherein:

the storage unit is operative to store an indication of particular cardiac signals to be stored in response to particular diagnostic triggers;

the sensing system is operative to sense cardiac signals;

the trigger-specific diagnostic selection unit is operative to identify the particular cardiac signals to be stored based on the trigger detected by the diagnostic trigger detection unit and by the indication of particular cardiac signals to be stored by the storage unit; and the trigger-specific signal storage controller is operative to control the storage of the particular cardiac signals identified by the diagnostic selection unit.

15. The system of claim 14 where the storage unit is operative to store pre-trigger cardiac signal data and wherein the trigger-specific cardiac signal storage controller is operative to selectively retain only those portions of stored pre-trigger cardiac signals corresponding to the indication of particular cardiac signals made by the trigger-specific diagnostic selection unit in response to particular diagnostic triggers.

16. A system for controlling the recording of cardiac signals within an implantable medical device capable of recording different types of cardiac signals in response to various diagnostic triggers, the system comprising:

means for storing an indication of particular cardiac signals to be stored in response to particular diagnostic triggers;

means for sensing cardiac signals within the patient;

means for detecting the occurrence of a trigger within the patient;

means for identifying, based on the particular detected trigger, the particular cardiac signals to be stored in response to the trigger including means for specifying, for each trigger, at least one combination of electrodes for sensing the cardiac signals to be stored; and means for storing the particular cardiac signals identified for storage by the means for identifying.

* * * * *